(12) United States Patent
Cauldwell et al.

(10) Patent No.: US 11,191,604 B2
(45) Date of Patent: Dec. 7, 2021

(54) SURGICAL INSTRUMENT WITH FASTENER PRELOAD LOCK-OUT

(71) Applicant: Davol Inc., Warwick, RI (US)

(72) Inventors: Nathan Stewart Cauldwell, Hope, RI (US); Donald E. Ziniti, Cumberland, RI (US); Derek Affonce, Uxbridge, MA (US); Justin Lewis, Taunton, MA (US); Augustus Felix, Cranston, RI (US); Talia D'Ambruoso, East Greenwich, RI (US)

(73) Assignee: Davol Inc., Warwick, RI (US)

( * ) Notice: Subject to any disclaimer, the term of this patent is extended or adjusted under 35 U.S.C. 154(b) by 335 days.

(21) Appl. No.: 16/508,157

(22) Filed: Jul. 10, 2019

(65) Prior Publication Data

US 2020/0015809 A1 Jan. 16, 2020

Related U.S. Application Data

(60) Provisional application No. 62/798,178, filed on Jan. 29, 2019, provisional application No. 62/697,354, filed on Jul. 12, 2018.

(51) Int. Cl.
*A61B 17/068* (2006.01)
*A61B 50/33* (2016.01)
(Continued)

(52) U.S. Cl.
CPC ............ *A61B 50/33* (2016.02); *A61B 17/068* (2013.01); *A61B 17/0682* (2013.01);
(Continued)

(58) Field of Classification Search
CPC . A61B 17/068; A61B 50/33; A61B 17/07207; A61B 17/0682; A61B 17/072;
(Continued)

(56) References Cited

U.S. PATENT DOCUMENTS 3,315,863 A 4/1967 O'Dea
4,881,544 A 11/1989 Green et al.
(Continued)

FOREIGN PATENT DOCUMENTS

AU 2013227990 A1 9/2013
EP 2 316 349 A1 5/2011
(Continued)

OTHER PUBLICATIONS

International Preliminary Report on Patentability for International Application No. PCT/US2019/041141, dated Jan. 21, 2021.
(Continued)

*Primary Examiner* — Julian W Woo
(74) *Attorney, Agent, or Firm* — Wolf, Greenfield & Sacks, P.C.

(57) ABSTRACT

A surgical instrument may include a handle and an elongated shaft extending distally from the handle. The surgical instrument may also include a fastener deployment system for deploying fasteners from the elongated shaft including a reciprocating driveshaft disposed within the elongated shaft. The fastener deployment system may include a follower disposed within the elongated shaft for displacing one or more fasteners within the elongated shaft towards a distal fastener deployment position. The surgical instrument may include a removable preload lock-out attached to the elongated shaft to prevent the follower from applying a preload to the fasteners.

40 Claims, 17 Drawing Sheets

(51) Int. Cl.
  *A61B 17/072* (2006.01)
  *A61B 17/00* (2006.01)
  *A61B 90/00* (2016.01)
  *A61B 17/128* (2006.01)

(52) U.S. Cl.
  CPC ...... *A61B 17/072* (2013.01); *A61B 17/07207* (2013.01); *A61B 17/1285* (2013.01); *A61B 2017/00367* (2013.01); *A61B 2017/00473* (2013.01); *A61B 2017/00477* (2013.01); *A61B 2017/07228* (2013.01); *A61B 2090/038* (2016.02); *A61B 2090/0801* (2016.02)

(58) Field of Classification Search
  CPC .. A61B 2090/0801; A61B 2017/00473; A61B 2090/038; A61B 2090/034; A61B 2017/0647; A61B 17/1285; A61B 2017/07228; A61B 2017/00367; A61B 2017/00477
  See application file for complete search history.

(56) References Cited

U.S. PATENT DOCUMENTS

| | | | |
|---|---|---|---|
| 5,366,133 | A | 11/1994 | Geiste |
| 5,415,335 | A | 5/1995 | Knodell, Jr. |
| 5,470,007 | A | 11/1995 | Plyley et al. |
| 5,718,359 | A | 2/1998 | Palmer et al. |
| 5,762,255 | A | 6/1998 | Chrisman et al. |
| 5,893,506 | A | 4/1999 | Powell |
| 6,605,047 | B2 | 8/2003 | Zarins et al. |
| 7,083,576 | B2 | 8/2006 | Zarins et al. |
| 7,147,140 | B2 | 12/2006 | Wukusick et al. |
| 7,452,327 | B2 | 11/2008 | Durgin et al. |
| 7,494,461 | B2 | 2/2009 | Wells et al. |
| 7,568,605 | B2 | 8/2009 | Kruszynski |
| 7,780,055 | B2 | 8/2010 | Scirica et al. |
| 8,225,979 | B2 | 7/2012 | Farascioni et al. |
| 8,397,972 | B2 * | 3/2013 | Kostrzewski ........ A61B 17/068 227/175.2 |
| 8,418,906 | B2 | 4/2013 | Farascioni et al. |
| 8,469,983 | B2 | 6/2013 | Fung et al. |
| 8,701,962 | B2 | 4/2014 | Kostrzewski |
| 8,967,445 | B2 | 3/2015 | Kostrzewski |
| 9,016,539 | B2 | 4/2015 | Kostrzewski et al. |
| 9,107,662 | B2 | 4/2015 | Kostrzewski |
| 9,155,537 | B2 | 10/2015 | Katre et al. |
| 9,232,944 | B2 | 1/2016 | Cappola et al. |
| 9,351,728 | B2 | 5/2016 | Sniffin et al. |
| 9,358,004 | B2 | 6/2016 | Sniffin et al. |
| 9,427,230 | B2 * | 8/2016 | Ranucci ............... A61B 17/068 |
| 9,474,578 | B2 | 10/2016 | Farascioni et al. |
| 9,706,993 | B2 | 7/2017 | Hessler et al. |
| 9,730,694 | B2 | 8/2017 | Scirica et al. |
| 9,775,611 | B2 | 10/2017 | Kostrzewski |
| 9,783,329 | B2 | 10/2017 | Sniffin et al. |
| 9,801,629 | B2 | 10/2017 | Farascioni et al. |
| 10,039,546 | B2 | 8/2018 | Williams et al. |
| 10,085,746 | B2 | 10/2018 | Fischvogt |
| 2005/0070758 | A1 | 3/2005 | Wells et al. |
| 2006/0226195 | A1 | 10/2006 | Scirica et al. |
| 2009/0008424 | A1 | 1/2009 | Green |
| 2011/0101066 | A1 | 5/2011 | Farascioni et al. |
| 2016/0192927 | A1 | 7/2016 | Kostrzewski |
| 2016/0270835 | A1 | 9/2016 | Reed |
| 2016/0354081 | A1 | 12/2016 | Ranucci et al. |
| 2017/0135696 | A1 | 5/2017 | Zhan et al. |
| 2019/0336126 | A1 | 11/2019 | Williams et al. |
| 2020/0015816 | A1 | 1/2020 | Cauldwell et al. |
| 2020/0015922 | A1 | 1/2020 | Cauldwell et al. |

FOREIGN PATENT DOCUMENTS

| | | |
|---|---|---|
| EP | 2 499 987 A2 | 9/2012 |
| EP | 3 042 618 A1 | 7/2016 |
| EP | 3 069 663 A1 | 9/2016 |
| WO | WO 2014/143525 A1 | 9/2014 |
| WO | WO 2014/163925 A1 | 10/2014 |
| WO | WO 2017/184505 A2 | 10/2017 |
| WO | WO 2018/118312 A1 | 6/2018 |

OTHER PUBLICATIONS

International Search Report and Written Opinion for International Application No. PCT/US2019/041141, dated Jan. 15, 2020.
PCT/US2019/041141, Jan. 15, 2020, International Search Report and Written Opinion.
U.S. Appl. No. 16/508,183, filed Jul. 10, 2019, Cauldwell.
U.S. Appl. No. 16/508,002, filed Jul. 10, 2019, Cauldwell.
PCT/US2019/041141, Nov. 13, 2019, Invitation to Pay Additional Fees.
Invitation to Pay Additional Fees for International Application No. PCT/US2019/041141, dated Nov. 13, 2019.
U.S. Appl. No. 17/228,884, filed Apr. 13, 2021, Cauldwell et al.

* cited by examiner

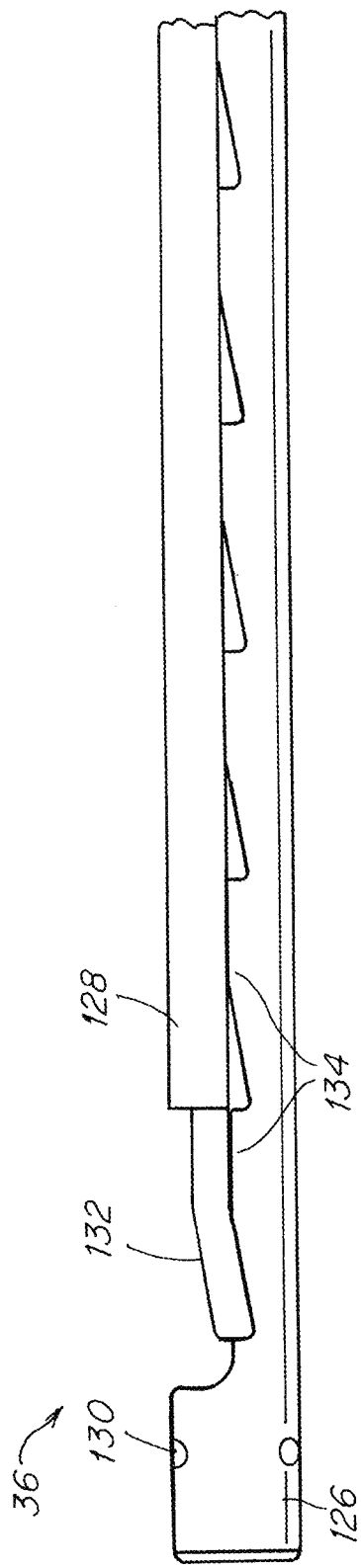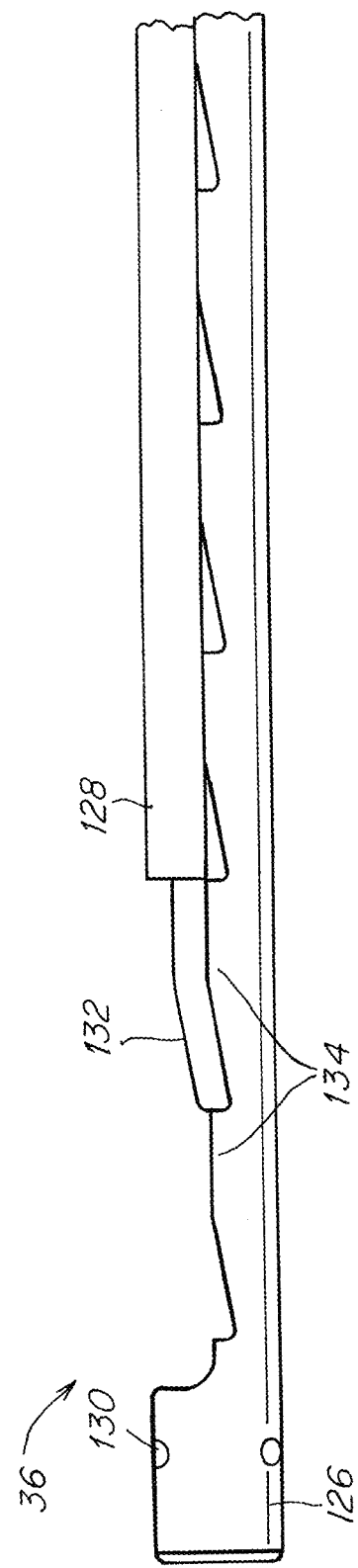

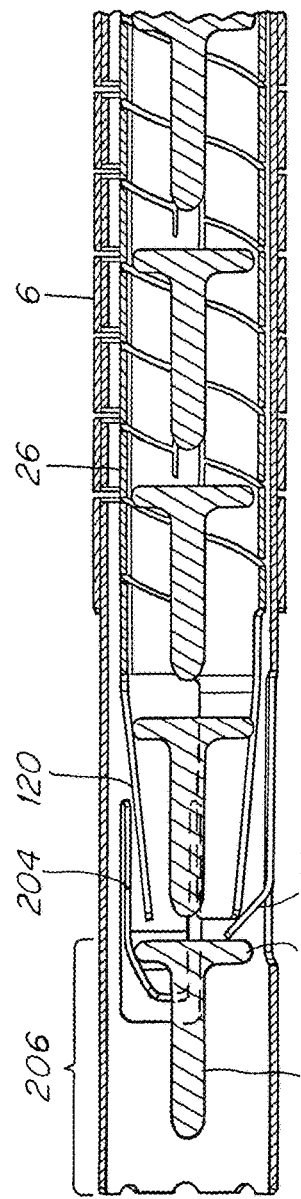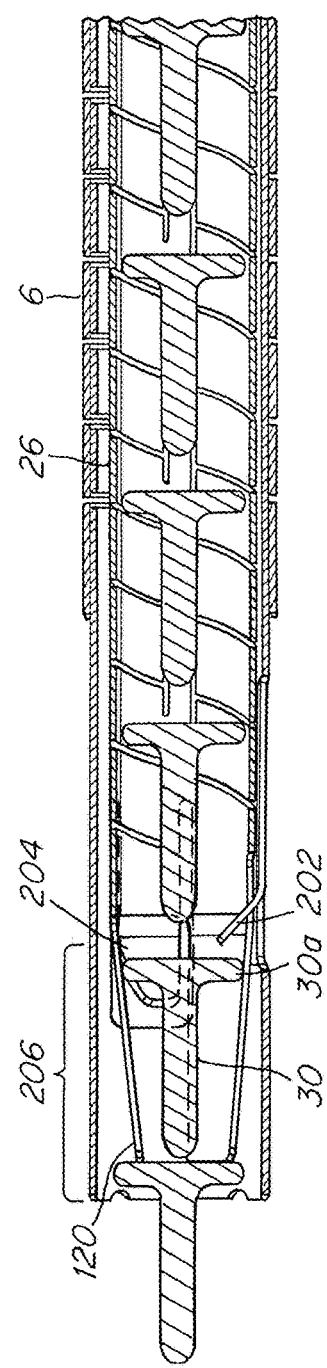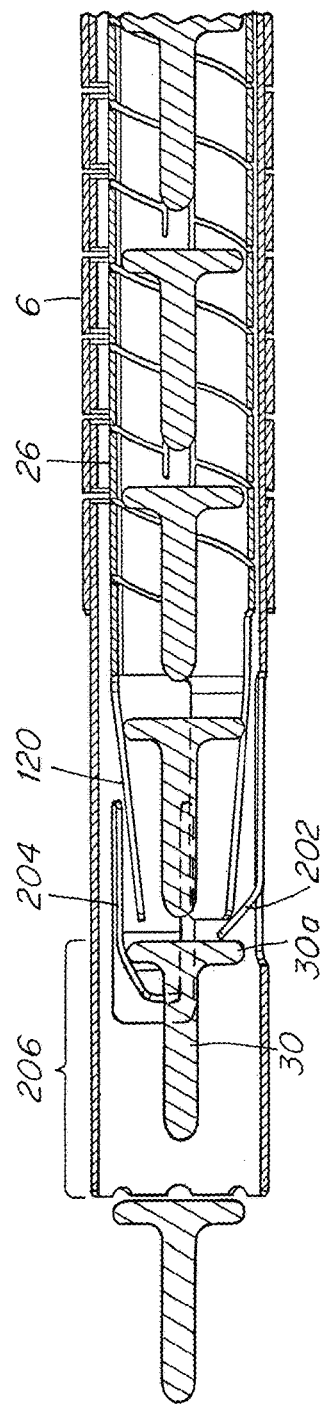

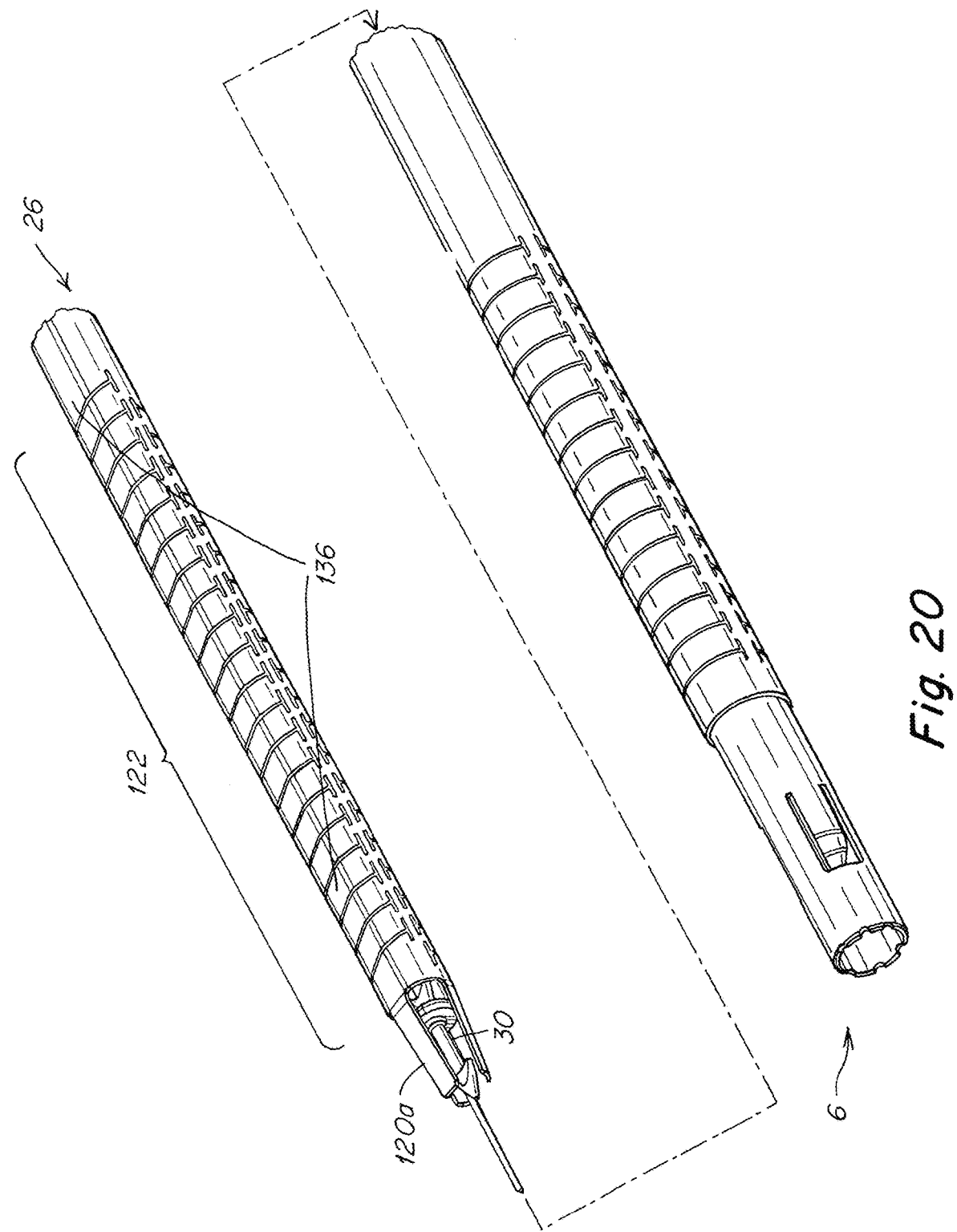

SURGICAL INSTRUMENT WITH FASTENER PRELOAD LOCK-OUT

RELATED APPLICATIONS

This application claims the benefit of U.S. Provisional Application No. 62/697,354, filed Jul. 12, 2018 and U.S. Provisional Application No. 62/798,178, filed Jan. 29, 2019. The entire contents of these applications are incorporated herein by reference in their entirety.

FIELD

Disclosed embodiments are related to a surgical instrument for deploying fasteners.

BACKGROUND

A surgical mesh fabric or other prosthetic repair fabric may be used to surgically repair a hernia. The prosthetic repair fabric is typically placed in an open procedure or laparoscopically. To secure the repair fabric in place, one or more fasteners may be deployed through the prosthetic repair fabric and into the underlying tissue. Oftentimes, surgical instruments used during the surgical repair of a hernia, or other appropriate procedure, include magazines, or other structures, that are capable of holding a plurality of fasteners for deployment from the surgical instrument. The inclusion of a plurality of fasteners within the surgical instrument may increase the speed of the procedure and may also reduce the need to remove and re-introduce the surgical instrument into a surgical field to provide additional fasteners.

SUMMARY

In one embodiment, a surgical instrument comprises a handle, an elongated shaft extending in a distal direction from the handle, at least one fastener located within the elongated shaft, a fastener deployment system configured to deploy the at least one fastener from the elongated shaft in response to actuation thereof, and a lock-out removably attached to the elongated shaft. The fastener deployment system is configured to apply a first load to the at least one fastener prior to actuation thereof. The lock-out is configured and arranged to prevent the fastener deployment system from applying the first load to the at least one fastener while the lock-out is attached to the elongated shaft.

In another embodiment, a method is provided of operating a surgical instrument. The method comprises acts of: (a) providing a surgical instrument including a handle, an elongated shaft extending in a distal direction from the handle, at least one fastener located within the elongated shaft, a fastener deployment system configured to deploy the at least one fastener from the elongated shaft in response to actuation thereof, the fastener deployment system configured to apply a first load to the at least one fastener prior to actuation thereof, and a lock-out attached to the elongated shaft to prevent the fastener deployment system from applying the first load to the at least one fastener. The method also comprises acts of (b) detaching the lock-out from the elongated shaft whereby the fastener deployment system applies the first load to the at least one fastener, and (c) following act (b), actuating the fastener deployment system to deploy the at least one fastener from the elongated shaft.

In another embodiment, a surgical instrument comprises a handle, an elongated shaft extending in a distal direction from the handle, a stack of fasteners located within the elongated shaft, a fastener deployment system configured to deploy at least one of the fasteners from the elongated shaft in response to actuation thereof, and a lock-out clip removably attached to an exterior surface of the elongated shaft. The elongated shaft includes an internal channel and a hole extending from the external surface to the internal channel. The stack of fasteners is located within the internal channel of the elongated shaft. The fastener deployment system includes a follower which has a pusher configured to engage and apply a first load to the stack of fasteners. The lock-out clip includes a pin extending through the hole in the elongated shaft and into the internal channel of the elongated shaft. The pin is located between the stack of fasteners and the pusher to prevent the pusher from applying the first load to the stack of fasteners while the lock-out is attached to the elongated shaft.

In another embodiment, a lock-out is provided for a surgical instrument including an elongated shaft, a stack of fasteners located within the elongated shaft, and a fastener deployment system to deploy a fastener from the elongated shaft. The fastener deployment system is configured to apply a preload to the stack of fasteners. The lock-out comprises a grip handle configured to be grasped and manipulated to attach and detach the lock-out to and from the elongated shaft, the grip handle including first and second sides. The lock-out further comprises a first pair of opposing clip fingers and a second pair of opposing clip fingers. The first and second pairs of clip fingers are configured to receive the elongated shaft therebetween and engage an exterior surface thereof. Each of the first and second pairs of clip fingers includes a first clip finger and a second clip finger, the first clip fingers being located at the first side of the grip handle and the second grip fingers being located at the second side of the grip handle. The first grip fingers are spaced a first distance from each other and the second grip fingers are spaced a second distance from each other, the first and second distances being different from each other.

In another embodiment, a lock-out is provided for a surgical instrument including an elongated shaft, a stack of fasteners located within the elongated shaft, and a fastener deployment system to deploy a fastener from the elongated shaft. The fastener deployment system is configured to apply a preload to the stack of fasteners. The lock-out comprises a grip handle and a pin extending from the grip handle. The grip handle is configured to be grasped and manipulated to attach and detach the lock-out to and from the elongated shaft. The pin is configured to cooperate with the fastener deployment system when the lock-out is attached to the elongated shaft. The lock-out further comprises a shroud configured to shield the pin from contact by a user when the lock-out is detached from the elongated shaft, and a pair of opposing clip fingers configured to receive the elongated shaft therebetween and engage an exterior surface thereof to detachably retain the lock-out on the elongated shaft.

In another embodiment, a surgical instrument system comprises a tray and a surgical instrument loaded in the tray. The surgical instrument includes a handle, an elongated shaft extending in a distal direction from the handle, a stack of fasteners located within the elongated shaft, and a fastener deployment system configured to deploy at least one of the fasteners from the elongated shaft in a distal direction in response to actuation thereof. The fastener deployment system is configured to engage and apply a first load to the stack of fasteners in the distal direction prior to actuation thereof. The surgical instrument system also comprises a lock-out removably attached to the elongated shaft and a tether coupling the lock-out to the tray so that the lock-out remains attached to the tray when the lock-out is detached from the elongated shaft. The lock-out is configured and arranged to prevent the fastener deployment system from applying the first load to the stack of fasteners while the lock-out is attached to the elongated shaft.

It should be appreciated that the foregoing concepts, and additional concepts discussed below, may be arranged in any suitable combination, as the present disclosure is not limited in this respect. The foregoing and other aspects, embodiments, and features of the present teachings can be more fully understood from the following description in conjunction with the accompanying drawings.

BRIEF DESCRIPTION OF DRAWINGS

The accompanying drawings are not intended to be drawn to scale. In the drawings, each identical or nearly identical component that is illustrated in various figures may be represented by a like numeral. For purposes of clarity, not every component may be labeled in every drawing. In the drawings:

FIG. 8A is a schematic representation of a distal portion of the anti-backup mechanism;

FIG. 8B is a schematic representation of the anti-backup mechanism depicted in FIG. 8A after one actuation cycle;

FIG. 19A is a cross-sectional view of the elongated shaft, reciprocating driveshaft, and fasteners in the unactuated position;

FIG. 19B is a cross-sectional view of the elongated shaft, reciprocating driveshaft, and fasteners depicted in FIG. 19A in the actuated position;

FIG. 19C is a cross-sectional view of the elongated shaft, reciprocating driveshaft, and fasteners depicted in FIG. 19A after actuation;

FIG. 20 is a schematic exploded view of the elongated shaft and the reciprocating driveshaft including a stack of fasteners;

DETAILED DESCRIPTION

Figure 1:
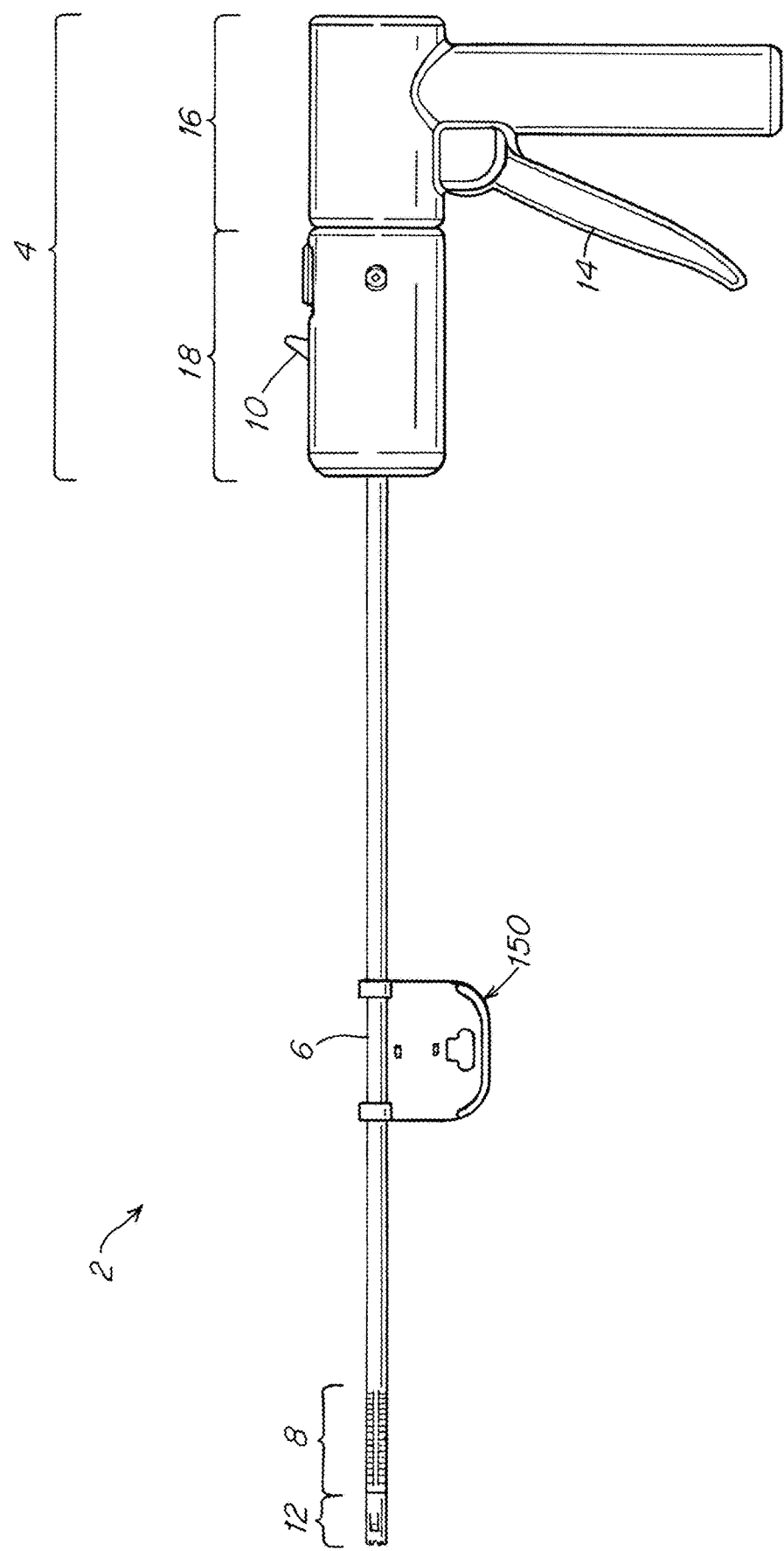
FIG. 1 is a schematic representation of a surgical instrument for deploying fasteners and includes a preload lock-out.

The inventors have recognized that the application of force, such as a preload, to a fastener for an extended period of time, such as during shipping and/or storage of a surgical instrument loaded with one or more fasteners, may adversely affect mechanical, structural and/or material properties and/or characteristics of the fasteners. For example, when subjected to a preload for an extended period of time prior to use of the surgical instrument, a stack of fasteners subjected to a preload may undergo deformation during accelerated aging.

In view of the foregoing, the inventors have recognized the benefits associated with preventing the application of a force to one or more fasteners, including a stack of fasteners, prior to using the surgical instrument for deploying the fasteners. In some embodiments, this force may be a preload applied to the stack of fasteners for facilitating fastener deployment. The above noted benefit may lead to improved consistency in fastener deployment and surgical instrument operation.

In one embodiment, the surgical instrument may include a handle and an elongated shaft extending in a distal direction from the handle. The elongated shaft may include a distally located fastener deployment position from which a fastener may be deployed at a distal end of the elongated shaft. The surgical instrument may also include a fastener deployment system to deploy a fastener from the fastener deployment position out of the distal end of the elongated shaft. The fastener deployment system may be embodied in any number of ways. Further, in some embodiments, the fastener deployment system may include a magazine, or other appropriate structure for containing a plurality of fasteners. Depending upon the particular embodiment, the plurality of fasteners may be arranged as a nested stack of fasteners, although other arrangements are also envisioned.

The fastener deployment system may be configured to preload the stack of fasteners with a force which is sufficient to facilitate deployment of the fasteners but yet less than the force required to deploy a fastener. For example, the application of a preload to the stack of fasteners in the distal direction may help maintain a distalmost fastener in the fastener deployment position, while also preventing movement of the stack of fasteners in the proximal direction away from the distal end of the shaft. In one embodiment, the fastener deployment system may include a follower, or other appropriate component, that is associated with the stack of fasteners such that it displaces one or more fasteners towards the fastener deployment position during an actuation cycle of the fastener deployment system.

The surgical instrument may be provided with a preloaded stack of fasteners. However, an extended period of time may pass from when the stack of fasteners is loaded into the instrument and actual use of the instrument for fastener deployment. For example, the fasteners may be loaded into the instrument during assembly by a manufacturer. An extended period of time may pass, such as many months or even longer, during which the instrument may reside in inventory, be shipped, and be stored at a user facility, such as a hospital, before the surgical instrument is eventually employed for fastener deployment. During this time, the fasteners may undergo deformation during accelerated aging and/or other physical or property changes when subjected to a constant preload.

In one embodiment, the surgical instrument may include a lock-out to reduce, and preferably prevent, the application of the preload on the stack of fasteners until the surgical instrument is to be used for deploying one or more fasteners. The lock-out may be attached to a portion of the elongated shaft suitable for interacting with the fastener deployment system in a manner which prevents the preload from being applied to the stack of fasteners. When it is desired to use the surgical instrument for deploying fasteners, the lock-out may be detached from the shaft to allow the fastener deployment system to apply the preload to the stack of fasteners prior to actuation of the instrument.

The lock-out may be configured as a clip which can be snapped on and off the elongated shaft. In one embodiment, the clip may include at least one pair of opposing clip fingers which are attachable to the shaft and an outwardly extending handle configured to be gripped and pulled to detach the clip from the shaft. The clip fingers may be configured to conform to the outer surface of the shaft. For example, in one embodiment, the clip fingers may have opposing curved shapes which correspond to the shape of the shaft. The clip fingers may have sufficient resilience or flexibility which permits the fingers to open and close for attaching and detaching the clip and gripping the elongated shaft therebetween.

As indicated above, the clip may be configured to interact with the fastener deployment system to lock-out and prevent a preload from being applied to the stack of fasteners until the instrument is used for fastener deployment. In one embodiment, the clip may include a pin or other suitable component which is associated with the fastener deployment system when the clip is attached to the elongated shaft. The pin may be arranged to extend inwardly from the clip and into an internal channel of the elongated shaft to prevent distal movement of the fastener deployment system toward the stack of fasteners. In one embodiment, the pin may be arranged to retain the follower in a spaced relation away from the stack of fasteners so that the follower does not engage and apply a preload or other force against the fasteners. Detaching the clip from the elongated shaft and removal of the pin from the internal channel allows the follower to move into engagement with and apply a preload force against the fasteners to move, if necessary, and hold the distalmost fastener in the fastener deployment position for subsequent fastener deployment upon actuation of the fastener deployment system.

The clip may be formed as a one-piece component although any suitable arrangement may be employed. The pin may be a separate component which is integrated with the clip. For example, in one embodiment, the pin may be insert molded to the clip. Such an arrangement allows the use of a pin fabricated from a relatively stronger material, such as a metal, as compared to the clip, which may be formed of a plastic material. However, the lock-out may be constructed in any suitable manner.

In some situations, the lock-out may be considered a sharp object due to the presence of a pin or similar component which could require disposal of the lock-out in accordance with a particular protocol for handling sharps. For example, the lock-out may need to be placed in a sharps container for subsequent disposal. To reduce the incidence of a potential contact by an individual handling the lock-out, it may be desirable to provide a cover or other suitable arrangement to shield the pin or other potential sharp component.

In one aspect, the lock-out may include a shroud configured to cover the clip fingers and the pin therein and thereby shield the pin from contact by an individual when the lock-out is detached from the shaft of the surgical instrument. The shroud may be configured to open and close so as to permit attachment and detachment of the lock-out to and from the shaft. When closed, the shroud may have a tubular-like configuration designed to wrap about the clip fingers as well as the elongated shaft when the lock-out is attached to the shaft.

For some situations, it may be desirable to avoid a loose component within a particular environment, such as an operating room. For example, a loose component within an operating room could potentially be dropped into a patient or otherwise become misplaced and require time to locate and account for the component. Thus, it may be desirable to avoid having a loose lock-out which potentially could become misplaced when it is detached from the shaft of the surgical instrument.

According to one aspect, the lock-out may be coupled to the packaging tray or a blister pack for the surgical instrument. When the lock-out is detached from the instrument to prepare the instrument for use, the lock-out will remain attached to the tray so that it will not become inadvertently misplaced during a surgical procedure. The lock-out may be coupled to the tray with a tether, such as a strap, having one end attached to the tray and its opposing end attached to the lock-out. The tether may be configured with a length which is sufficient to permit removal and manipulation of the instrument while also maintaining the detached lock-out in relatively close proximity to the tray so that the lock-out does not dangle from the tray when it is detached from the instrument.

Because the lock-out may be considered a sharp object, it may be desirable to detach the lock-out from the tray to facilitate its proper disposal following surgery. For example, the tether may be cut or detached from either the tray or the lock-out to detach the lock-out from the tray. In one embodiment, the lock-out may be configured to facilitate its detachment from the tether. The lock-out may include a slot or other suitable relief configured to permit removal of the tether, for example, by slipping the tether through the slot and from the lock-out.

In addition to deploying the fastener, actuation of the fastener deployment system may also result in the distal displacement of the follower so as to distally displace the stack of fasteners towards the fastener deployment position and position a next distalmost fastener in the fastener deployment position. The fastener deployment system may displace the follower in any appropriate fashion. For example, in one embodiment, the follower may be associated with a driveshaft of the fastener deployment system such that distal displacement of the driveshaft distally displaces the follower. Proximal movement of the follower may also be prevented through the use of an anti-backup element associated with the follower. Regardless of the specific manner in which the follower is displaced, the follower may be arranged and adapted to provide a controlled force to the stack of fasteners during displacement. The force applied to the stack of fasteners may be any appropriate force, and in one embodiment may be less than the actuation force applied to deploy a fastener from the fastener deployment position.

In certain embodiments, the follower may be constructed in any appropriate fashion such that it applies similar forces to the stack of fasteners during subsequent actuation cycles of the fastener deployment system. For example, the follower may include a driver which is associated with the fastener deployment system such that actuation of the fastener deployment system distally displaces the driver. The driver may also be associated with a compressible elastic component which is associated with a pusher. The elastic component may be adapted and arranged to provide a controlled force to the pusher upon displacement of the driver. The elastic component may comprise a coil spring, a conical spring, a pneumatic spring, an appropriately shaped component made of a compressible material (e.g. rubber), or any other appropriately shaped and sized compressible component capable of applying a force to the stack of fasteners when it is compressed. In some embodiments, in addition to providing a controllable force to the stack of fasteners, the elastic component may be sufficiently flexible to permit the follower to pass through an articulated portion of the elongated shaft while still applying a force to the stack of fasteners. In such an embodiment, the driver, elastic component, and pusher may also be sized and shaped to pass through the elongated shaft in both the straight and articulated configuration.

While the embodiments described herein refer to, and depict, the driver, elastic component, and pusher as separate components that are physically associated with one another, the current disclosure is not limited to the use of separate components. For example, in some embodiments, the driver, elastic component, and pusher may be provided as part of an integral component.

In some embodiments, the follower may be adapted to provide similar forces to the stack of fasteners during subsequent actuation cycles. Although this may be accomplished in any number of ways, in one embodiment, the follower may operate in the following manner. Upon actuation of the fastener deployment system, the driver may be distally displaced. The distal displacement of the driver may compress the elastic component from a first length to a compressed second length. Subsequent to compressing the elastic component, the elastic component may expand from the compressed second length to the original first length. As the elastic component expands to the second length, the fasteners may be distally displaced along the elongated shaft towards the fastener deployment position. In some embodiments, the difference between the first length and the second length may correspond to the length of one fastener. When the elastic component is in the expanded state corresponding to the first length, the elastic component may apply a first force to the pusher and the stack of fasteners. Subsequently, when the elastic component is in the compressed state corresponding to the second length, the elastic component may apply a second force to the pusher and the stack of fasteners. As would be expected for a compressed elastic component, the second force is greater than the first force. In some embodiments, the first force may be approximately zero. However, in other embodiments, it may be desirable to provide a distal bias to the stack of fasteners throughout the actuation cycle to prevent backwards or proximal movement of the stack of fasteners. In such an embodiment, the first force may be greater than zero and correspond to an initial compression of the elastic component prior to actuation of the fastener deployment system.

In addition to the forces applied to the stack of fasteners by the follower, restraining forces may also be applied to the stack fasteners to prevent distal movement of the fasteners until the force applied by the follower exceeds a preselected threshold force. For example, a first restraining force may be applied to the stack of fasteners prior to, and during, actuation of the fastener deployment system. The first restraining force may be applied to the stack of fasteners to oppose the first force applied to the stack of fasteners by the follower. Consequently, prior to actuation of the fastener deployment system, the stack of fasteners may remain stationary within the elongated shaft. However, during actuation, the elastic component may be compressed to a second compressed length to apply a greater force to the stack of fasteners as noted above. Once the applied force (e.g. the second force) is greater than the first restraining force, the stack of fasteners may be distally displaced by the follower to position the next fastener in the fastener deployment position. A second restraining force may subsequently be applied to restrain the stack of fasteners from additional distal movement during that actuation cycle.

Each of the noted restraining force may be provided by one or more restraints. Further, the restraints may be embodied in any number of fashions. For example, the restraints may include: one or more tabs that extend inwards and distally relative to the elongated shaft; detent arrangements; and other appropriate features. Further, the restraints may be integrally formed with the elongated shaft, or the restraints may be formed separately and subsequently assembled with the elongated shaft using any appropriate fashion including, but not limited to, welding, soldering, brazing, adhesives, mechanical couplings, fasteners, and interference fits.

In some embodiments, in addition to providing the restraining forces to the stack of fasteners, the restraints may also be used to define the fastener deployment position. For example, a head, or other appropriate feature, of a fastener may be retained between the first and second restraints to define the fastener deployment position.

In addition to providing a follower to control the forces applied to the stack of fasteners, as noted above, it may be desirable to provide a mechanism for maintaining the orientation of the fasteners within the elongated shaft as the stack of fasteners is displaced towards the fastener deployment position by the follower. In one embodiment, a guide surface may be sized and shaped to interact with a corresponding surface on at least a portion of the fasteners to maintain the orientation of the fasteners as they move within the elongated shaft. In some instances, the corresponding surface on the fastener may be shaped such that it is complementary both in shape and size to the guide surface. The guide surface may be positioned on any appropriate component of the elongated shaft, or a component that is disposed within the elongated shaft, that interacts with the fasteners as they are moved through the elongated shaft. Further, the guide surface may extend along a distal portion of the component, a portion of the component corresponding to the stack of fasteners, or the entire length of the component as the current disclosure is not limited as to the location and extent of the guide surface.

It should be understood that the guide surface and the corresponding surfaces on the fasteners may include any combination of appropriate shapes and/or features that are capable of maintaining the orientation of the fasteners. For example, the guide surface and the corresponding surfaces on the fasteners may include: corresponding flats; a protrusion and corresponding groove; and other complementary arrangements as should be apparent to one of ordinary skill in the art.

In one particular embodiment, the fasteners may be disposed within an internal channel of a reciprocating driveshaft that reciprocates in a proximal and distal direction. Further, the guide surface may be incorporated with the interior surface of the channel. In such an embodiment, the guide surface may interact with the corresponding surface of the fasteners to maintain an orientation of the fasteners within the reciprocating driveshaft. During actuation of the fastener deployment system, the driveshaft may be moved in a distal direction to deploy a fastener prior to moving in a proximal direction in preparation for the next actuation cycle. During this reciprocating movement of the driveshaft, the driveshaft may be moved relative to the stack of fasteners. Additionally, during, or subsequent to deployment of the fastener, the stack of fasteners may be displaced towards the distal end of the driveshaft to position the next distalmost fastener in the fastener deployment position using any appropriate biasing element. For example, the stack of fasteners may be displaced using a follower as described herein. As the stack fasteners are displaced towards the fastener deployment position, and as the driveshaft is moved relative to the stack of fasteners disposed therein, the guide surface may maintain the fasteners in a preselected orientation relative to one another and the driveshaft. As previously noted, maintaining the fasteners in a preselected orientation relative to one another and the driveshaft ensures proper alignment of the fasteners and may lower the necessary force to move the fasteners through an articulated portion of the elongated shaft.

For the sake of clarity, the currently disclosed embodiments are directed to a laparoscopic device. However, the current disclosure is not limited to laparoscopic devices. Instead, the currently disclosed lock-out, followers, restraints, and guide surfaces could be used in any appropriate device for the deployment of a fastener into tissue. For example, any of the currently disclosed components, or combination of disclosed components, could be incorporated into an endoscopic device, a borescopic device, a catheter, a surgical instrument for use in "open" procedures, or any other appropriate surgical instrument. Additionally, the surgical instrument may be loaded with one or more fasteners prior to being provided to an end user, or it may be constructed to allow the user to load the instrument with one or more fasteners. Further, while the various embodiments depicted herein are described as being used with a specific fastener, any appropriate fastener could be used with the currently disclosed embodiments including a tack, a clip, a staple, a pin, a tissue anchor, a bone anchor, or any other appropriate type of fastener.

Turning now to the figures, specific embodiments of the surgical instrument are described.

Figure 2:
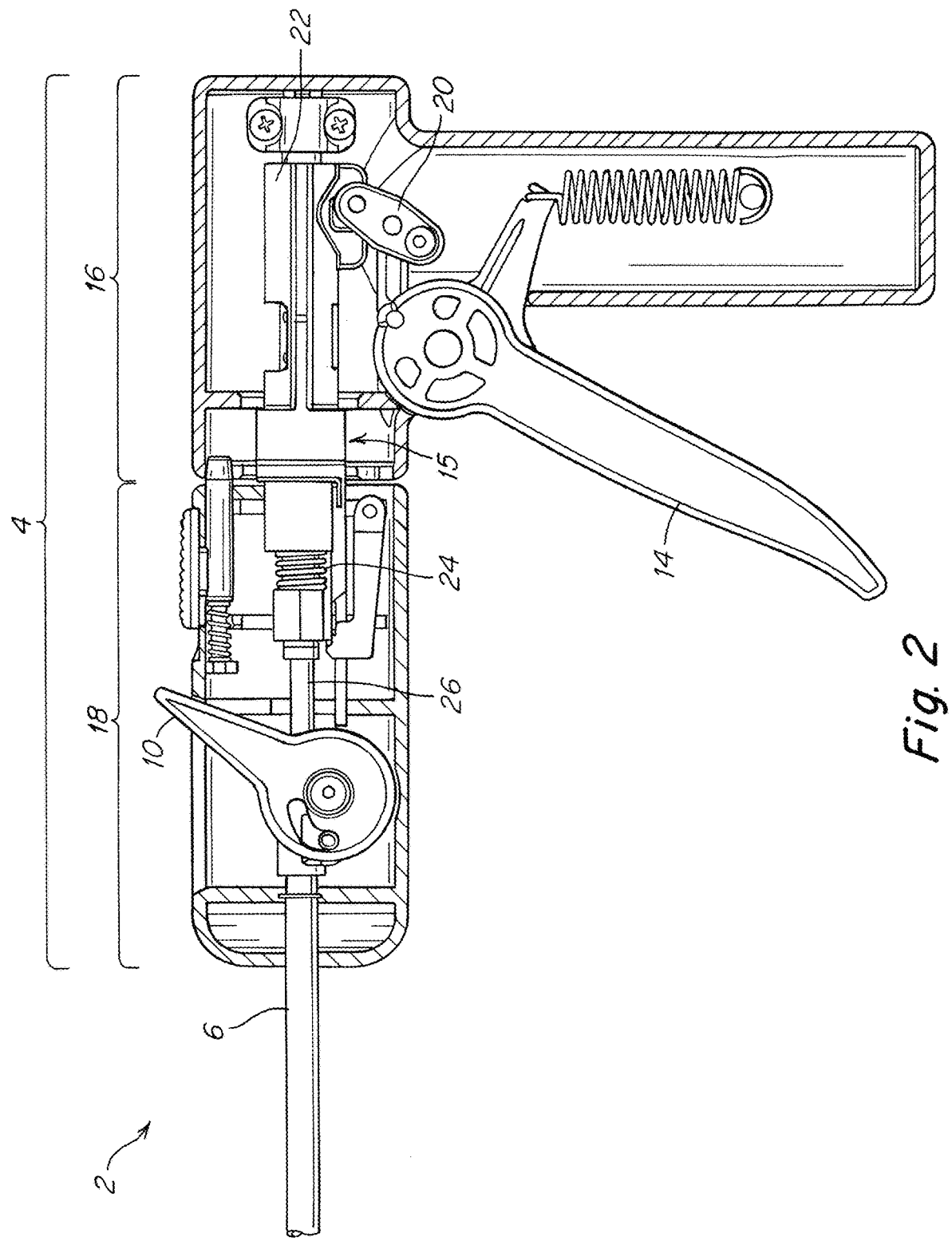
FIG. 2 is a schematic representation of the interior of the surgical instrument handle of FIG. 1.

FIG. 1 illustrates one embodiment of a surgical instrument 2 for deploying one or more surgical fasteners. The surgical instrument includes a handle 4 and an elongated shaft 6 extending distally from the handle 4. In addition to fasteners being deployed from a distal end of the elongated shaft, the elongated shaft 6 may include an articulable portion 8. A trigger 14 may be provided on the handle to actuate an associated fastener deployment system 15, as shown in FIG. 2, and deploy a fastener into tissue. The surgical instrument may also include a lock-out 150 to prevent the fastener deployment system from applying a force, such as a preload, to fasteners carried by the instrument until fastener deployment is desired using the instrument.

As illustrated, and as described in more detail below, the lock-out 150 may be attached to a portion of the elongated shaft associated with the fastener deployment system 15 to prevent a preload from being applied to the fasteners. When it is desired to use the surgical instrument for deploying fasteners, the lock-out 150 may be detached from the shaft to allow a preload to be applied to the fasteners prior to actuation of the instrument.

The fastener deployment system 15 may be embodied in any number of different ways. However, in the particular embodiment depicted in FIG. 2 the fastener deployment system may include a trigger 14, a rigid linkage 20, a shuttle 22, a power assist device 24, and a reciprocating driveshaft 26 as well as other components that are not depicted. Actuation of the trigger 14 may distally displace the rigid linkage 20 to distally displace the shuttle 22 and store energy in the power assist device 24. After a preselected amount of actuation, the power assist device 24 may release the stored energy to distally accelerate the driveshaft 26 and deploy a fastener from the distal end of the elongated shaft 6.

While a particular power assist device 24 is depicted, the power assist device 24 may correspond to any appropriate construction capable of aiding in deploying a fastener from the elongated shaft 6 of the surgical instrument. Depending on the particular embodiment, the power assist device 24 may supply all of the power necessary to deploy a fastener in response to actuation of the trigger 14, or it may only supply a portion of the power necessary to deploy a fastener. In one specific embodiment, the power assist device 24 may correspond to the power assist device disclosed in application Ser. No. 13/804,043, entitled POWER ASSIST DEVICE FOR A SURGICAL INSTRUMENT, filed on Mar. 14, 2013. While a surgical instrument including a power assist device has been depicted, in some embodiments, the surgical instrument 2 may not include a power assist device, in which case actuation of the trigger 14 may displace the driveshaft 26, either directly or indirectly through the use of an appropriate transmission, to deploy a fastener from a distal end of the elongated shaft 6.

Figure 3:
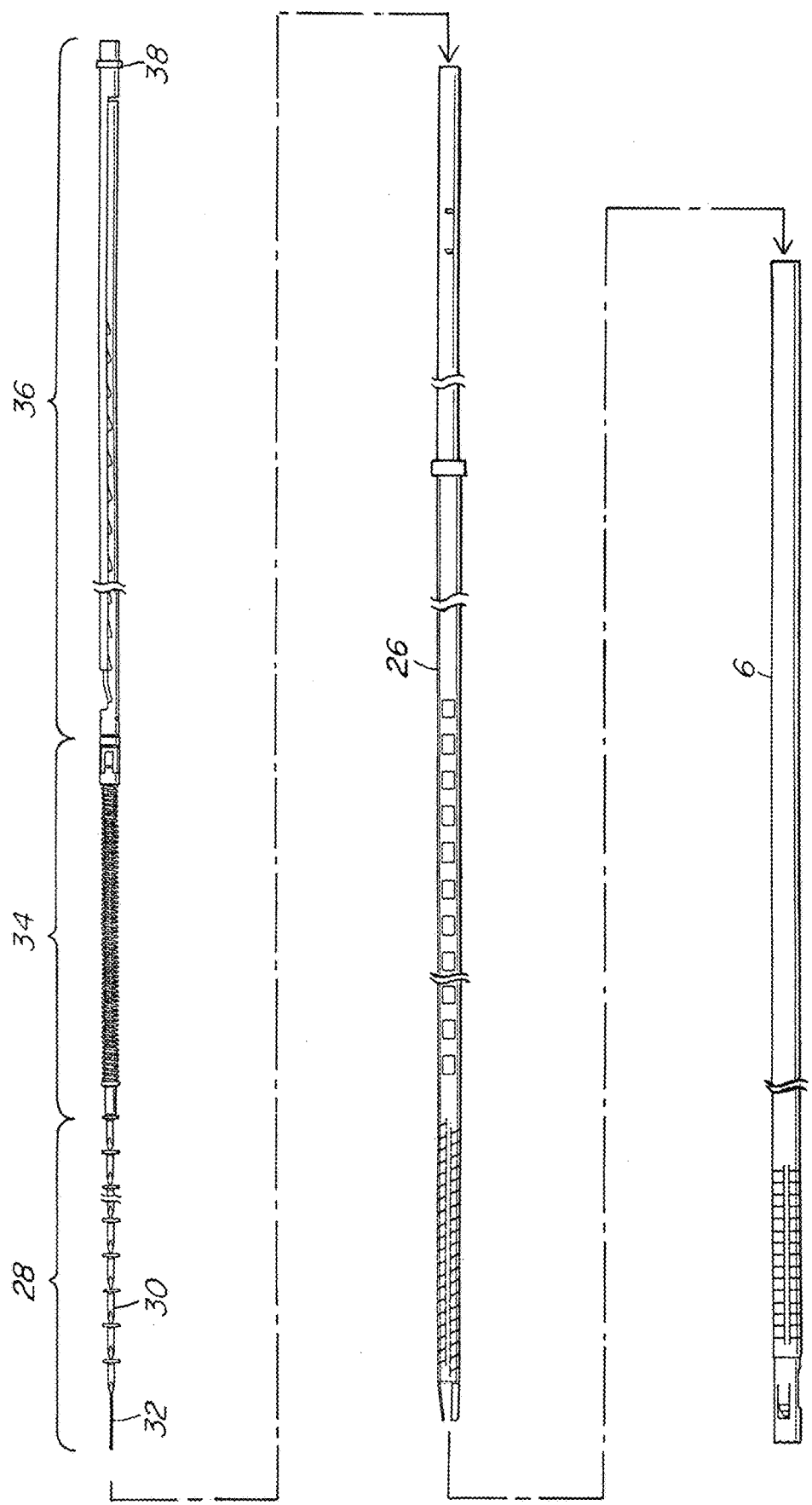
FIG. 3 is a schematic exploded view of the elongated shaft and the components disposed within the channel of the elongated shaft.

FIG. 3 presents an exploded view of one embodiment of the elongated shaft 6 and the various components disposed within the elongated shaft. In the depicted embodiment, the driveshaft 26 is located within the elongated shaft 6. As illustrated by FIGS. 2 and 3, when disposed within the elongated shaft 6, the driveshaft 26 extends proximally from the elongated shaft 6 into the handle 4. The surgical instrument also includes a stack of fasteners 28, a follower 34, and an anti-backup element disposed within an internal channel of the driveshaft 26. The follower and/or the anti-backup element may be associated with or part of the fastener deployment system. The stack of fasteners 28 may include one or more fasteners 30, and in some instances may be a plurality of fasteners 30.

In addition to the above components, the surgical instrument may also include a fastener guide 32 to help maintain the alignment of the stack of fasteners 28, the follower 34, and the anti-backup element 36 within the internal channel of the driveshaft 26. While any appropriate structure may be used, in the depicted embodiment, the fastener guide 32 is a distally extending wire positioned in approximately the center of the channel of the driveshaft. The fastener guide 32 may be retained within the channel in any appropriate fashion. For example, the fastener guide 32 may be attached to a portion of the anti-backup element 36, a portion of the handle 4, or any other appropriate structure. Further, the faster guide 32 may be attached using any appropriate method including, but not limited to, adhesives, mechanical interference, clamping, soldering, brazing, and welding.

Upon actuation of the trigger, the fastener deployment system may be actuated resulting in a distal displacement of the driveshaft 26. As described in more detail below, a distal displacement of the driveshaft 26 deploys a distalmost fastener located in the fastener deployment position. The driveshaft 26 also distally displaces the follower 34 so as to displace the stack of fasteners 28 and position the next distalmost fastener in the fastener deployment position. The follower 34 and anti-backup element 36 may be associated such that a distal displacement of the follower 34 results in the anti-backup element extending in the distal direction to prevent a proximal movement of the follower 34. After deployment of a fastener, and positioning of the next fastener in the fastener deployment position, the driveshaft 26 may be moved in a proximal direction to prepare the surgical instrument for the next actuation while preventing proximal movement of the stack of fasteners 28, the follower 34, and the anti-backup element 36.

Figure 4:
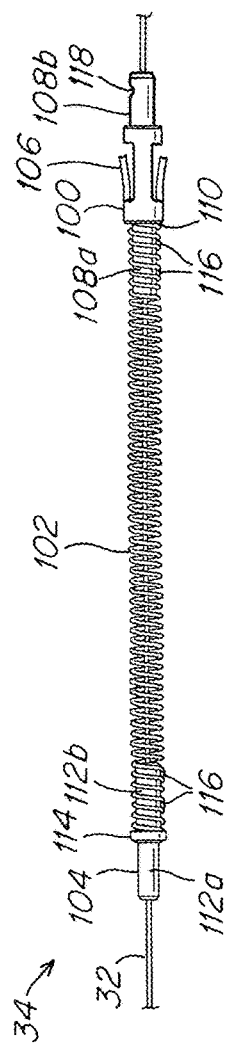
FIG. 4 is a schematic representation of a follower.
Figure 5:
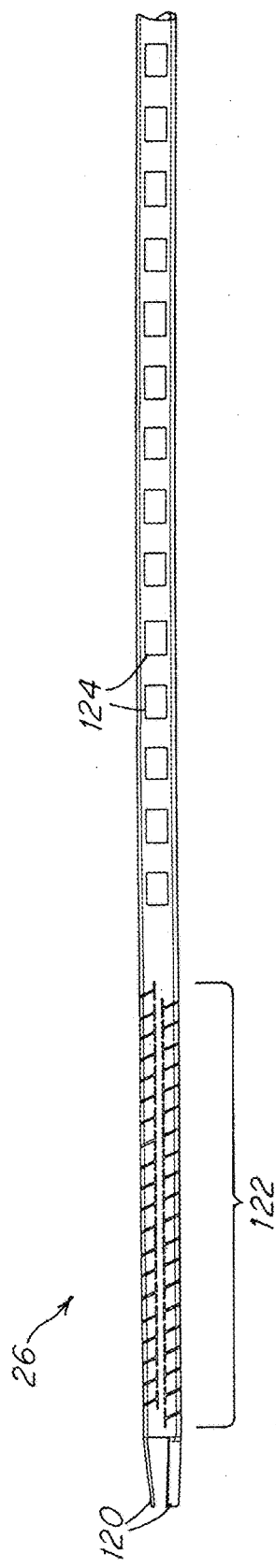
FIG. 5 is a schematic representation of a distal portion of the reciprocating driveshaft.
Figure 6:
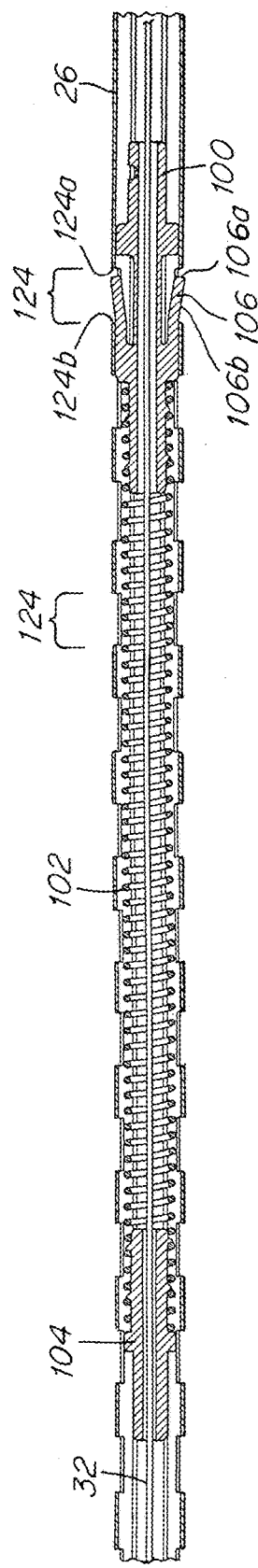
FIG. 6 is a schematic cross-sectional view of the follower located within the driveshaft.

The interaction between the follower 34 and the driveshaft 26 is depicted in FIGS. 4-6.

In the depicted embodiment, the follower 34 includes a driver 100, an elastic component 102, and a pusher 104. The driver 100 is adapted to interact with the driveshaft 26 to displace the follower 34 in a distal direction. The driver 100 includes tabs 106 which interact with openings 124 on the driveshaft 26. The tabs 106 may be flexible and extend outwards and distally from the driver 100. In addition, the tabs 106 may be sized, shaped, and arranged such that the tabs 106 may be disposed within the openings 124 as the driver 100 is distally moved through driveshaft 26. The driver 100 may also include a distal portion 108a as well as a shoulder 110. The distal portion 108a and the shoulder 110 may be sized and shaped to retain a distal end of the elastic component 102 on the distal portion 108a. The distal portion 108a may also include one or more retention features 116. As illustrated, the retention features 116 may be protrusions located on the distal portion 108a that interfere with the elastic component 102 to retain the elastic component thereon. Alternatively, the elastic component 102 may be retained on the driver 100 using any appropriate method including, but not limited to, mechanical interference, interlocking features, adhesives, welding, soldering, and brazing. The driver 100 may also include a coupling 118 located on a proximal portion 108b. The coupling 118 may be adapted and arranged to attach the follower 34 to the anti-backup element 36.

In one embodiment, the elastic component 102 is a coil spring that extends between the driver 100 and the pusher 104. As noted above, while a coil spring has been depicted, other springs and appropriate components could be used in place of a coil spring. Regardless of the specific component used as the elastic component 102, the elastic component 102 may be sized, shaped, and arranged to be associated with both the driver 100 and the pusher 104. Further, due to the use of a spring, or other appropriate compressible component, as the driver is moved in a distal direction, the elastic component 102 is compressed to apply a force to the pusher 104. Larger displacements of the driver 100 prior to movement of the pusher 104 may result in larger compressions of the elastic component 102 and correspondingly larger forces. Depending upon the particular embodiment, the elastic component 102 may exhibit a linear force to displacement relationship, or a nonlinear force to displacement relationship, as the current disclosure is not limited in this fashion.

Similar to the driver 100, the pusher 104 may include a proximal portion 112b and a shoulder 114 that are sized and shaped to retain a distal end of the elastic component 102. The pusher 104 may also include one or more retention features 116 for retaining the elastic component 102 similar to those described above for the driver 100. The pusher 104 may also include a distal portion 112a that is adapted and arranged to apply a force to the most proximally located fastener of the fastener stack. In some embodiments, the distal portion 112a may directly contact at least the proximal most fastener in the stack of fasteners, though embodiments in which the distal portion 112a indirectly applies a force to the stack of fasteners are also envisioned.

As depicted in FIG. 5, the driveshaft 26 may include one or more fastener drivers 120 located on the distal end of the driveshaft 26. In some embodiments, the fastener driver 120 may be one or more flexible tabs that extend inwards and distally from the distal end of the driveshaft 26. The fastener drivers 120 may be adapted to apply a force to a fastener located in the fastener deployment position to deploy the fastener from the distal end of the elongated shaft. The driveshaft may also include a flexible portion 122 to accommodate movement of the reciprocating driveshaft through the articulable portion of the elongated shaft. In the depicted embodiment, the flexible portion 122 is formed by providing a pattern of slots, or cuts, in the driveshaft 26. As noted above, the driveshaft 26 may also include openings 124 that are sized and shaped to accommodate the tabs 106 of the driver 100 in an expanded position. One or more sets of openings 124 may be axially spaced along one or more surfaces of the driveshaft 124. In some embodiments, the axial spacing between the openings 124 may correspond to the length of a single fastener. In the current embodiment, two sets of openings 124 extend along opposite sides of the driveshaft 26 to accommodate both of the tabs 106 of the driver 100. The openings 124 may extend along the entirety of driveshaft 24, or as depicted in the figures, the openings 124 may extend along a portion of the driveshaft 24 corresponding to an initial proximal position of the follower 34 and a final distal position of the follower 34 after all of the fasteners have been deployed from the surgical instrument.

Having described the corresponding features on the driveshaft 26 and the follower 34, the interactions of these two components during actuation in one possible embodiment will now be described with reference to FIG. 6. Prior to actuation, the tabs 106 of the driver 100 may be located in the expanded state in any one of the corresponding openings 124 of the driveshaft 26. While the tabs 106 are in the expanded state within a corresponding opening 124, a proximal portion of the driveshaft 124a, such as a proximal edge of the opening may be axially aligned with a proximal aspect 106a of a tab 106. Consequently, as the driveshaft 26 is moved in a distal direction during actuation, the proximal driveshaft portion 124a applies a distally directed force to the proximal aspect 106a of the tabs 106 resulting in a distal displacement of the driver 100. After the fastener has been deployed, the driveshaft 26 is subsequently moved in a proximal direction. During the proximal movement of the driveshaft 26, a distal portion of the shaft 124b, such as a distal edge of the openings 124, may be drawn over an exterior aspect 106b, such as an exterior surface, of the tabs. As described in more detail below, the driver 100 may be prevented from moving backwards during the relative movement of the driveshaft 26 and the driver 100. Further, as noted above, the tabs 106 are flexible. Thus, as the distal driveshaft portion 124b is drawn over the exterior aspect 106b of the tabs, the tabs 106 may be displaced inwards and out of the openings 124 to permit the relative movement of the driver 100 and the driveshaft 26. The proximal displacement of the driveshaft 26 may be continued until the tabs 106 are aligned with the next distally located set of openings 124 and the tabs 106 are in the expanded state within the openings 124. Subsequent actuation cycles may result in the driver 100 progressively moving in a distal direction as the driver 100 engages with the next corresponding set of openings 124 of the driveshaft. In view of the above, the driver 100 of the follower 34 and the driveshaft 26 may be described as forming two separate components of a walking beam assembly that is configured to sequentially displace the follower 34 in a distal direction during each actuation cycle of the fastener deployment system.

Figure 7A:
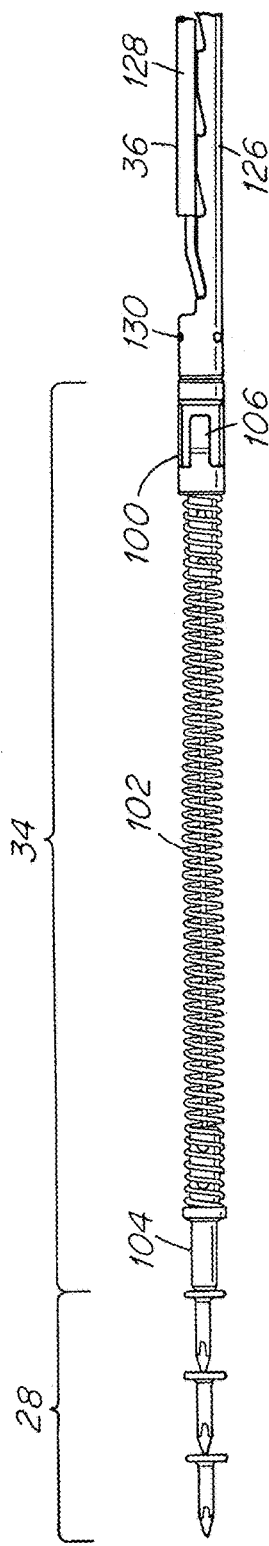
FIG. 7A is a schematic representation of a stack of fasteners and the follower in an unbiased position.
Figure 7B:
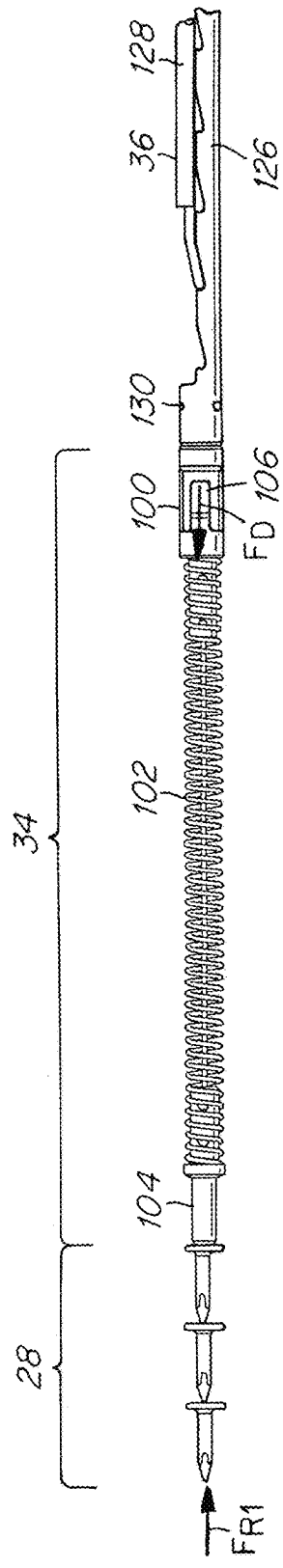
FIG. 7B is a schematic representation of the stack of fasteners and the follower of FIG. 6 with a biasing force applied.

FIGS. 7A-7B depict the interaction of the stack of fasteners 28, the follower 34, and the anti-backup element 36 during an actuation cycle of the fastener deployment system. As illustrated in the figures, the pusher 104 may be in contact with a proximally located fastener of the fastener stack 28. The elastic component 102 may also be associated with a proximal portion of the pusher 104 and a distal portion of the driver 100. The driver 100 may be coupled to a rack arm 126 of the anti-backup element 36 by a coupling 130. The driver 100 and rack arm 126 may be coupled in such a manner that distal movement of the driver 100 may result in the distal extension of the rack arm 126 relative to a pawl arm 128 of the anti-backup element 36. Thus, as the follower 34 is distally displaced through the elongated shaft, the anti-backup element 36 correspondingly elongates. Consequently proximal movement of the follower 34 may be prevented by the anti-backup element 36 throughout the actuation cycle. As depicted in the figures, coupling 130 corresponds to a pin connection. However, any appropriate connection may be used including, but not limited to, interlocking mechanical features, a set screw, fasteners, adhesives, welding, brazing, and interference fits.

Prior to actuation, as depicted in FIG. 7A, the elastic component 102 of the follower 34 is in the expanded state corresponding to the first length and may apply a first distally directed force to the distally located pusher 104 and the stack of fasteners 28. The follower 34 and the stack of fasteners 28 are prevented from moving in a proximal direction by the anti-backup element 36. In the depicted embodiment, the anti-backup element 36 includes a rack arm 126 which may be moved in the distal direction, and a pawl arm 128 which remains stationary during actuation of the surgical instrument.

Figure 7C:
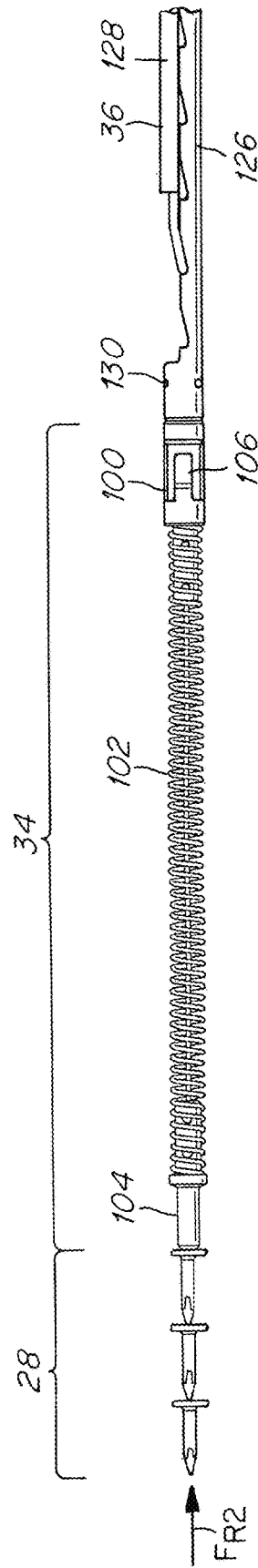
FIG. 7C is a schematic representation of the stack of fasteners and the follower of FIG. 6 after the stack of fasteners have been distally displaced.

Referring to FIG. 7B, as the fastener deployment system is actuated, the driveshaft, not depicted, may apply a force $F_D$ to the tabs 106 of the driver 100 which drives the driver 100 in a distal direction as described above. A proximally directed first restraining force $F_{R1}$ may be applied to the stack of fasteners 28. Initially, the first restraining force $F_{R1}$ may be equal to force $F_D$. Thus, during the initial portions of actuation, the stack of fasteners 28 may remain stationary resulting in the compression of elastic component 102 between the pusher 104 and the driver 100. As actuation continues, the force applied to the driver 100 may continue to increase as the elastic component 102 is further compressed. This continued compression of the elastic component 102 applies an increasing distally directed force to the stack of fasteners 28. At some point during actuation, the spring may be compressed to a second length corresponding to the elastic component 102 applying a second distally directed force to the pusher 104 and the associated stack of fasteners 28. This second distally directed force may be greater than the first restraining force $F_{R1}$ resulting in the expansion of the elastic component 102 and distal displacement of the pusher 104 and associated stack of fasteners 28, see FIGS. 7B-7C.

As depicted by the figures, the elastic component 102 continues to expand from the second length to the first length as the stack of fasteners 28 is displaced in the distal direction. As the elastic component 102 approaches the expanded first length, a proximally directed second restraining force $F_{R2}$ may be applied to the stack of fasteners 28 to prevent further distal movement of the stack of fasteners. The second restraining force $F_{R2}$ may be greater than the first restraining force to oppose both the force applied to the stack of fasteners 28 by the elastic component 102 as well as possible kinetic energy stored in the stack of fasteners 28 and follower 34 as they are being distally displaced. The second restraining force may also be less than the actuation force to deploy a fastener from the elongated shaft. In some embodiments, the second restraining force $F_{R2}$ may be applied once a distally located fastener of the stack fasteners 20 has been positioned in the fastener appointment position. After the stack of fasteners 28 has been distally displaced and the fastener deployment system has been reset, the surgical instrument may be actuated again resulting in further distal displacement of the follower 34 and the associated stack of fasteners 28.

In addition to displacement of the follower 34 and the associated stack of fasteners 28, actuation of the fastener deployment system may also result in an extension of the anti-backup element 36 as noted above. More specifically, due to the driver 100 and the rack arm 126 being coupled, distal displacement of the driver 100 may result in a corresponding distal displacement of the rack arm 126 relative to the pawl arm 128. The distal movement of the rack arm 126 may extend the anti-backup element 36 in a distal direction to prevent backwards movement of the driver 100 after the stack of fasteners 28 has been distally displaced. The interactions of the rack arm 126 and the pawl arm 128 are illustrated in more detail in FIGS. 8A and 8B. Teeth 134 may be spaced along the axial length of the rack arm 126. A corresponding pawl 132 may be positioned on a distal portion of the pawl arm 128. The pawl 132 and the corresponding teeth 134 may be adapted and arranged to permit distal movement of the rack arm 126 in response to distal movement of the driver. The pawl 132 and the corresponding teeth 134 may also be adapted and arranged to prevent proximal movement of the rack arm 126. In one embodiment, the distance between the teeth 134 may be approximately equal to one fastener length. However, embodiments in which the distance between teeth 134 is a fraction of a fastener length, or greater than a fastener length, are also envisioned. In addition to the above, while a rack and pawl system have been depicted for the anti-backup element 36, any appropriate mechanism capable of preventing backwards movement of the follower and the stack fasteners could be used.

As indicated above, the follower is 34 is configured and arranged to apply a distally directed preload to the stack of fasteners to drive the stack of fasteners toward the distal end of the shaft and maintain the distalmost fastener in the fastener deployment position. For some applications, it may be desirable to employ a lock-out prevent the preload from being applied to the fasteners until it is desired to use the instrument for fastener deployment.

Figure 9A:
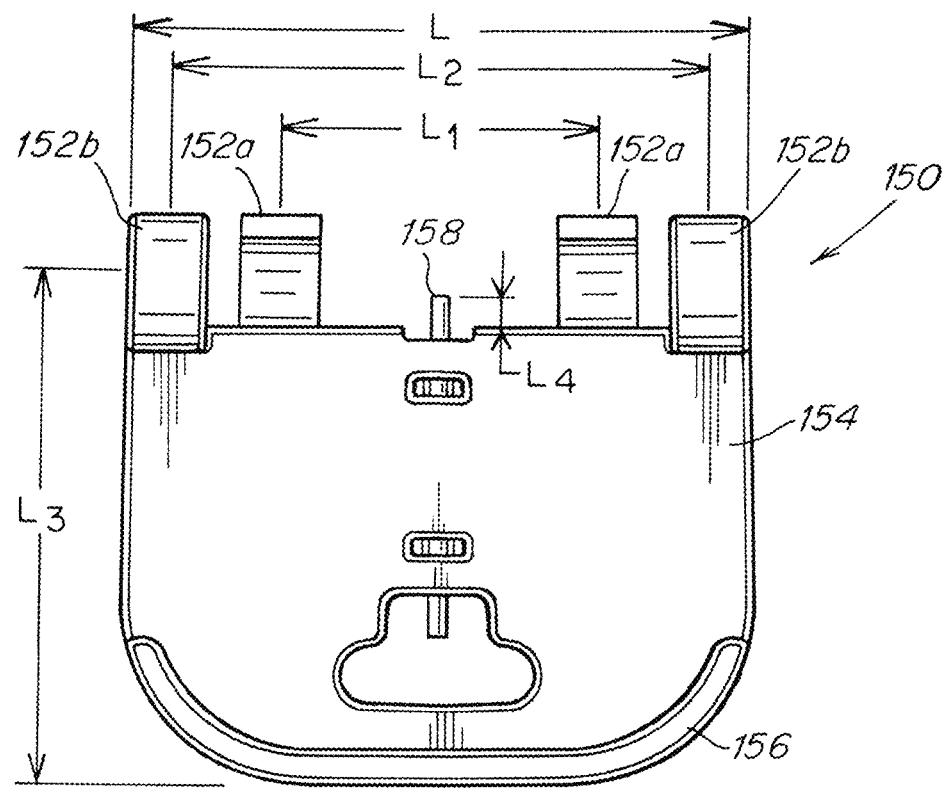
FIG. 9A is a schematic front view of a preload lock-out.
Figure 9B:
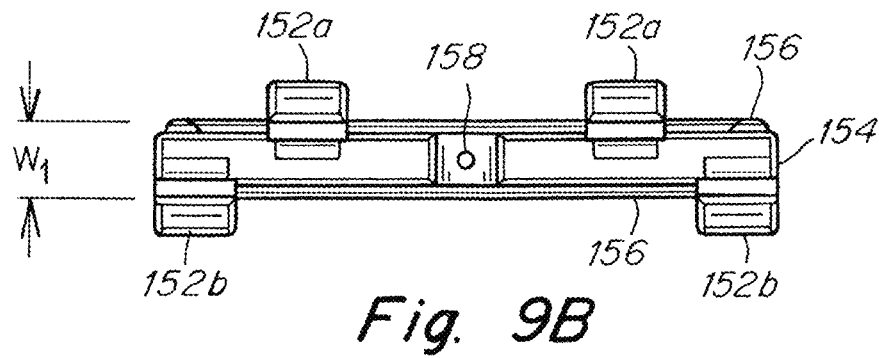
FIG. 9B is a schematic top view of the preload lock-out of FIG. 9A.
Figure 10:
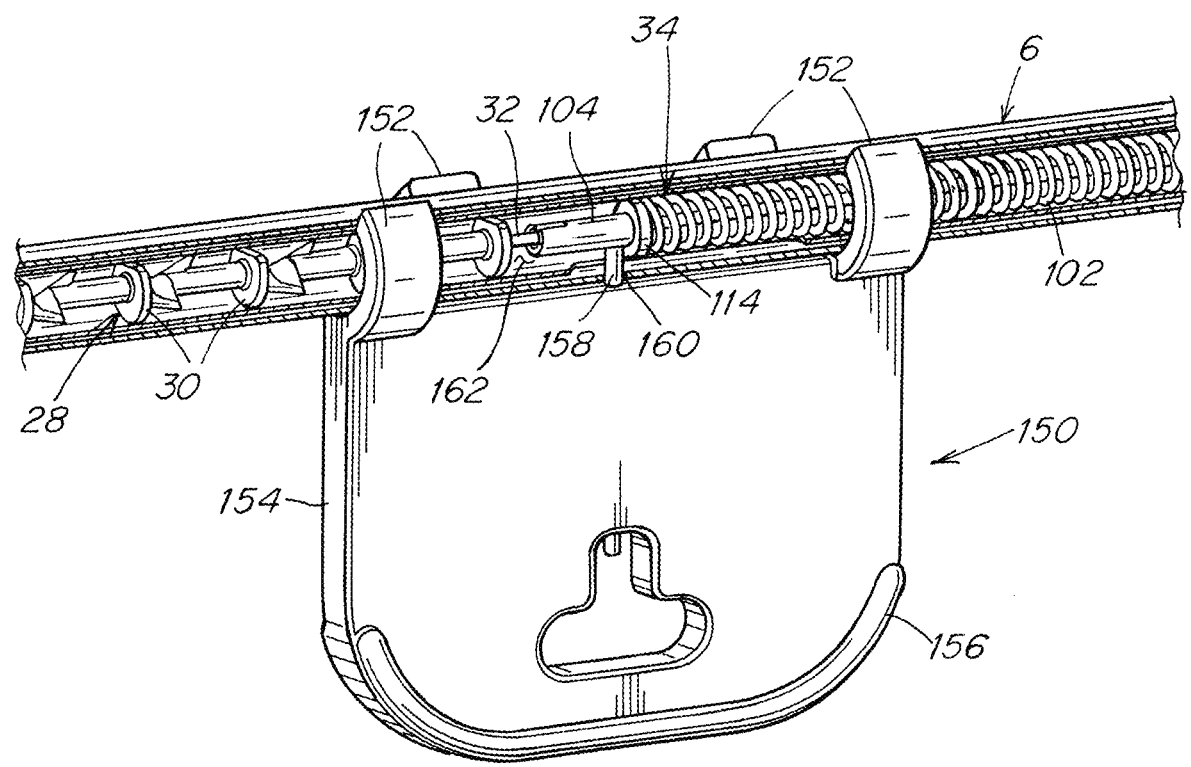
FIG. 10 is a schematic perspective view of the lock-out attached to the elongated shaft of the surgical instrument of FIG. 1 illustrating the lock-out preventing the follower from applying a preload to the fasteners.

In one embodiment shown in FIGS. 9A-10, the lock-out 150 may be configured as a clip which can be mounted on and removed from the elongated shaft. As illustrated, the clip 150 may include two pairs of opposing first clip fingers 152a and second clip fingers 152b which are attachable to the shaft 6 and an outwardly extending grip handle 154 configured to be grasped and pulled to detach the clip from the shaft. One or more features may be provided to enhance the user's ability to grasp the grip handle pull the lock-out from the shaft. In one embodiment, one or more raised ribs 156 may extend about at least a portion of the outer periphery of the grip handle. It is to be appreciated that other suitable grip features may be utilized as should be apparent to one of skill in the art.

The clip fingers 152a, 152b may be configured to conform to the outer surface of the shaft 6. For example, in one embodiment, the clip fingers 152a, 152b may have opposing curved shapes which correspond to the shape of the shaft. The clip fingers may have sufficient resilience or flexibility which permits the fingers to open and close for attaching and detaching the clip and gripping the elongated shaft therebetween. Although illustrated as having two pairs of opposing clip fingers, it should be understood that the lock-out may include any number of clip fingers, including a single pair, or more than two pairs. Moreover, other suitable arrangements for attaching and detaching the lock-out to the elongated shaft may be employed as should be apparent to one of skill in the art.

The grip fingers may be arranged in any suitable configuration to facilitate attachment and detachment of the lock-out relative to the elongated shaft. As shown in FIGS. 9A-9B, the clip fingers may be arranged with the first fingers 152a provided on a first side of the lock-out being spaced apart by a first length $L_1$ and the second fingers 152b provided on a second opposite side of the lock-out being spaced apart by a second length $L_2$ which is different from the first length $L_1$. In one embodiment, the first length $L_1$ between the first fingers 152a is less than the second length $L_2$ between the second fingers 152b. As illustrated, the first fingers 152a may be located inward of the second fingers 152b, and the second fingers 152b may be located at opposite ends of the lock-out.

The lock-out 150 may also include a pin 158 which is configured to cooperate with the fastener deployment system when the clip is attached to the elongated shaft. As illustrated in FIG. 10, the pin 158 may be arranged to extend inwardly from the grip handle 154, through a corresponding hole 160 in the elongated shaft 6, and into an internal channel 162 of the shaft to prevent distal movement of the fastener deployment system toward the fasteners. In one embodiment shown in FIG. 10, the pin 158 may be arranged to maintain the follower 34 in a spaced relation away from the stack of fasteners 28 so that the follower does not engage and apply a preload or other force against the fasteners. More particularly, the clip is positioned so that the pin 158 extends through the shaft and is located between the stack of fasteners 28 and the follower 34 with the pin 158 engaging the shoulder 114 of the distally biased pusher 104. Detaching the clip 150 from the elongated shaft and removal of the pin 158 from the internal channel allows the pusher 104 to move into engagement with the proximal-most fastener 30 and apply a preload force against the stack of fasteners 28 for subsequent fastener positioning and deployment upon actuation of the fastener deployment system.

In one exemplary embodiment, the lock-out may have an overall length L of about 1.25 inches with the first fingers 152a spaced apart by a length $L_1$ of about 0.65 inches and the second fingers being spaced apart by a length $L_2$ of about 1.09 inches. The clip fingers 152 may be configured with a curvature having an inner diameter of about 0.22 inches with the free ends of the fingers being spaced apart by a width $W_1$ about 0.15 inches. The grip handle 154 may have a length L3 from the center of the clip fingers of about 1.18 inches. The pin 158 may have a diameter of about 0.03 inches and extend from the surface of the grip handle by a length $L_4$ of about 0.07 inches. It is to be understood that the lock-out dimensions are exemplary and that the lock-out may employ any suitable shape and/or sizes as should be apparent to one of skill in the art.

As indicated above, the lock-out may be considered a sharp object due to the presence of the pin 158 or similar component which could require disposal of the lock-out in accordance with a particular protocol for handling sharp objects. For example, the lock-out may need to be placed in a sharps container for subsequent disposal. To reduce the incidence of a potential contact by an individual handling the lock-out, it may be desirable to provide a cover or other suitable arrangement to shield the pin or other potential sharp component.

Figure 11A:
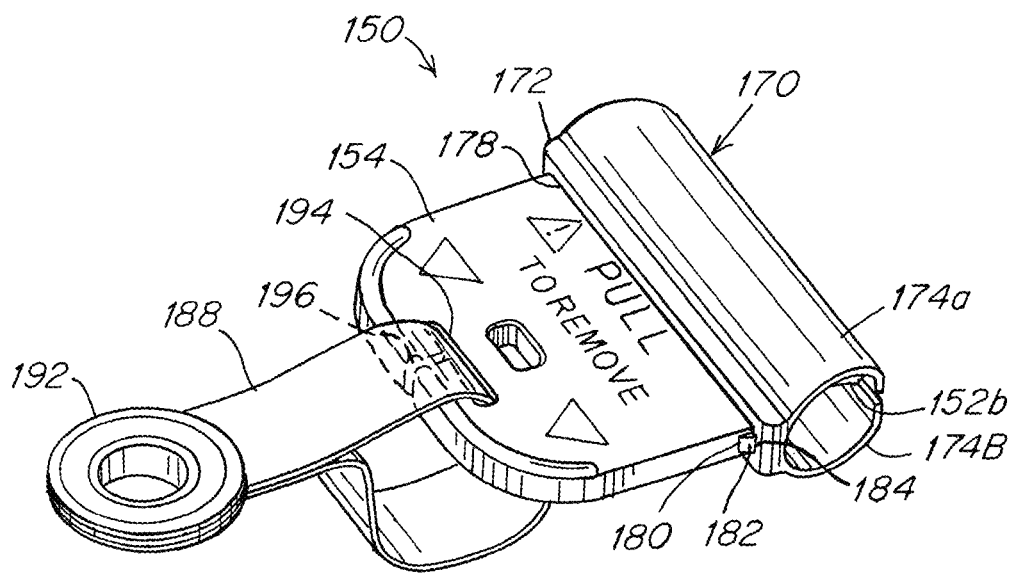
FIGS. 11A-11C are schematic perspective views of the lock-out with a shroud for shielding the lock-out pin and a tether for attaching the lock-out to a tray.
Figure 11B:
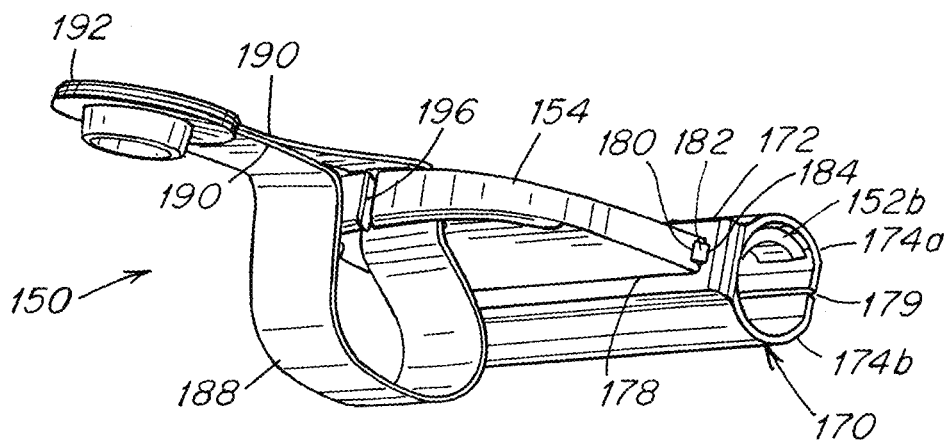
Figure 11C:
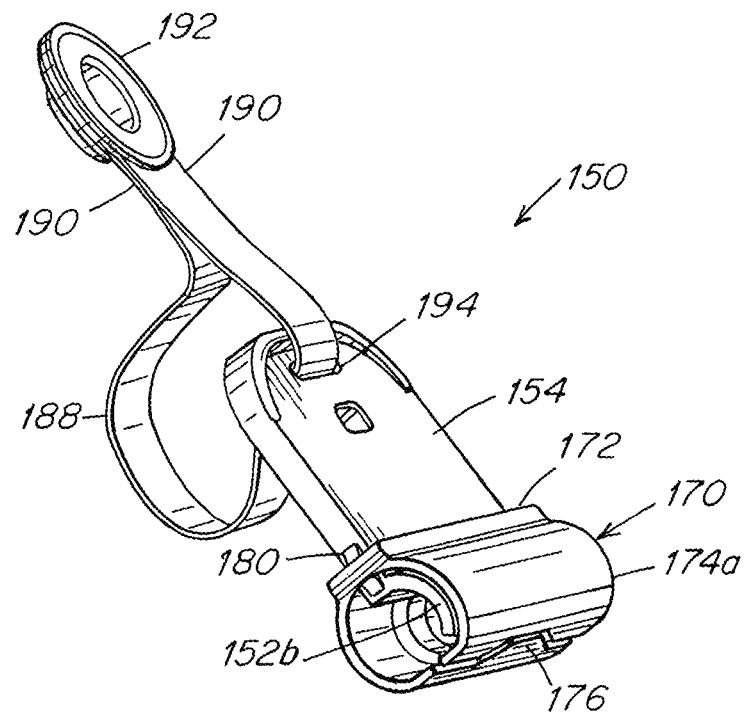

In one illustrative embodiment shown in FIGS. 11A-11C, the lock-out 150 may include a shroud 170 configured to cover and shield the pin 158 from contact by an individual when the lock-out is detached from the elongated shaft 6 of the surgical instrument. The shroud may be configured to open and close so as to readily permit attachment and detachment of the lock-out to and from the shaft. When closed as shown in the figures, the shroud 170 may have a tubular-like configuration designed to wrap about and cover the clip fingers 152a, 152b as well as the elongated shaft 6 when the lock-out is attached to the shaft.

The shroud 170 may include a base 172 and a pair of shroud segments 174a, 174b extending from the base which can be opened relative to the clip fingers for attaching and detaching the lock-out, and closed to encompass the clip fingers and the pin when the lock-out is attached to and detached from the shaft. Each shroud segment 174a, 174b may have an arcuate shape configured to form approximately 180° of the tube-like structure when the shroud is in the closed configuration.

Figure 12:
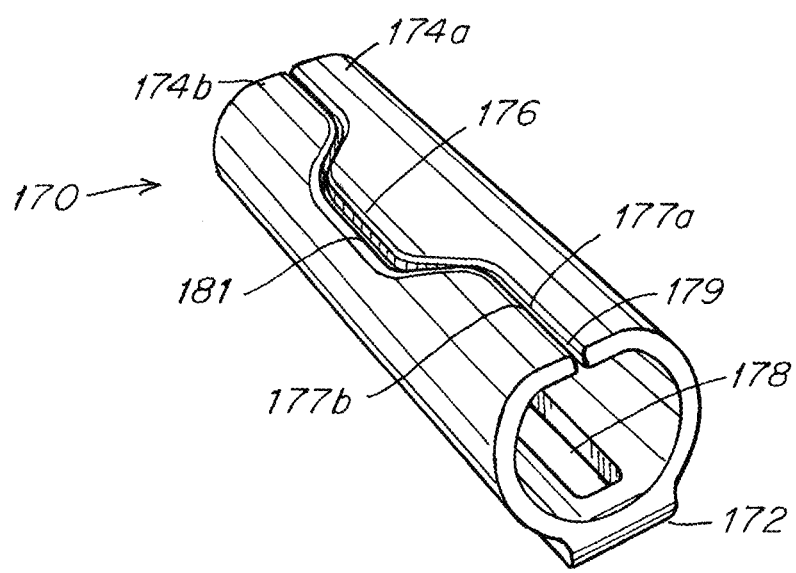
FIG. 12 is a schematic perspective view of the shroud for the lock-out of FIGS. 11A-11C.

In one embodiment shown in FIG. 12, at least a portion of one of the shroud segments 174a may extend beyond 180° to form an extension 176, such as a tongue, which is configured to cover the pin should the shroud segments be collapsed inwardly toward the pin when the lock-out is detached from the elongated shaft. The opposing shroud segment 174b may include a recess 181 configured to receive the extension 176 when the shroud segments are closed. As illustrated, the free ends 177a, 177b of the shroud segments may be positioned in close proximity to each other in the closed position to form a relatively narrow gap 179 therebetween.

The shroud 170 may be fabricated as a separate component which can be coupled to the lock-out 150. In one embodiment illustrated in FIGS. 11A-11C, the shroud 170 may be configured so that the base 172 is located adjacent the end of the lock-out handle 154 with the shroud segments 174a, 174b extending from the base and about the clip fingers 152a, 152b. As shown in FIG. 12, the base may include a slot 178 or other suitable opening configured to slidably receive the grip handle 154 therethrough to position the shroud on the lock-out.

The lock-out may include one or more locking features to maintain the shroud in its desired position. In one embodiment illustrated in FIGS. 11A-11C, a pair of locks 180 may be provided on opposite sides of the grip handle 154 in proximity to the clip fingers to engage the base 172 when the shroud is positioned on the lock-out. Each lock 180 may include a cam-like configuration which facilitates placement of the shroud into position between the locks and the clip fingers, and thereafter restricts movement of the shroud away from the clip fingers. In one embodiment, each lock 180 may include a ramp-like surface 182 which facilitates sliding the shroud over the locks in a direction toward the clip fingers and into position, and an abutment 184 at the end of the ramp-like surface which is configured to abut the base and act as a stop to restrict movement of the shroud in a direction away from the clip fingers. It is to be appreciated that any suitable lock arrangement may be employed as should be apparent to one of skill in the art.

The shroud 170 may be formed to have a flexible configuration which facilitates opening and closing the shroud segments, as well as placement of the shroud on the lock-out. In this manner, the shroud is not required to grasp and hold the elongated shaft of the instrument as done by the clip fingers. However, if desired, the shroud segments could be configured to assist with holding the lock-out on the shaft as should be apparent to one of skill in the art.

In one embodiment, the shroud may be formed from a material which is conducive to providing flexible characteristics. For example, and without limitation, the shroud may be molded from a polyurethane or polyethylene material, although other suitable materials may be used as should be apparent to one of skill in the art.

For some situations, it may be desirable to avoid having a loose component within a particular environment, such as an operating room. For example, a loose component could potentially become misplaced and require time to locate and account for the component. Thus, it may be desirable to avoid having a lock-out which potentially can become misplaced when it is detached from the shaft of the surgical instrument.

In one embodiment, the lock-out may be coupled to a packaging tray or blister pack of the surgical instrument. When the lock-out is detached from the instrument to prepare the instrument for use, the lock-out will remain attached to the tray so that it will not become inadvertently misplaced during a surgical procedure.

Figure 13:
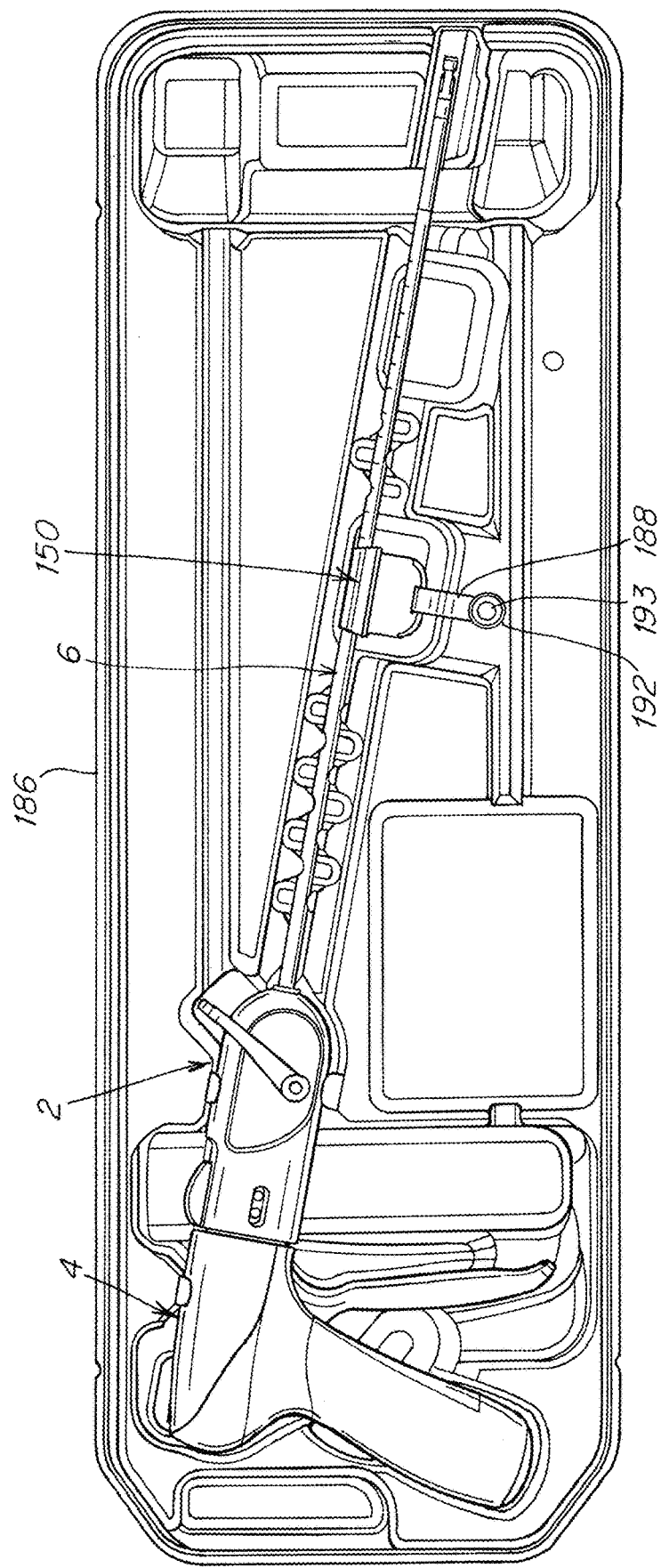
FIG. 13 is a schematic top view of a surgical instrument loaded in a tray with the preload lock-out coupled to the tray with the tether.

In one embodiment illustrated in FIG. 13, the lock-out 150 may be coupled to the tray 186 using a tether 188 having one end attached to the tray and its opposing end attached to the lock-out. As shown in FIGS. 11A-11C, the tether 188 may include a strap formed as a loop with the free ends 190 of the strap coupled together with a grommet 192, or other suitable component, which may be attached to the tray with a fastener 193, such as a rivet. The looped-end of the strap may be coupled to the grip handle 152 of the lock-out. In one embodiment, the strap 188 may be looped through a hole 194, such as a slot or other suitable opening, in the grip handle.

The tether 188 may be configured with a length which is sufficient to permit removal and manipulation of the instrument while also maintaining a detached lock-out in relatively close proximity to the tray so that the lock-out does not dangle excessively from the tray when it is detached from the instrument. In one embodiment, the tether may have a length of about 1.75 inches, although a tether of any suitable length may be employed as should be apparent to one of skill in the art.

Because the lock-out may be considered a sharp object, it may be desirable to detach the lock-out from the tray to facilitate its disposal following a procedure. If desired, the tether may be cut or detached from either the tray or the lock-out to remove the lock-out from the tray. For some applications, the lock-out may be configured to facilitate its separation from the tether.

In one embodiment illustrated in FIGS. 11A-11B, the lock-out 150 may include a slot 196 (shown in phantom in FIG. 11A) or other suitable passage configured to permit removal of the tether, for example, by slipping the tether from the lock-out. As shown, the slot 196 may be configured to extend from the hole 194 in the grip handle, which is used for attaching the tether 188 to the lock-out, through the outer periphery of the grip handle. The slot 196 may be oriented transverse to the hole 194 and have a width sufficient to accommodate the thickness, but not the width, of the tether to permit the tether to be slipped through the slot when the tether and the lock-out are manipulated relative to each other so that the edge of the tether can be slid into and through the slot. In one embodiment, the slot 196 may be oriented perpendicular to the hole 194. It is to be appreciated that other suitable arrangements may be employed for detachably coupling the lock-out to the tether as should be apparent to one of skill in the art.

The lock-out may be attached to the elongated shaft during assembly of the surgical instrument to minimize the period of time that the stack of fasteners would be subjected to a preload. However, it is to be appreciated that the lock-out may be attached to the surgical instrument at any appropriate time as should be apparent to one of skill in the art.

In one embodiment, the lock-out may be attached by initially displacing the pusher 104 of the follower 34 in the proximal direction away from the stack of fasteners and against the biasing force of the spring 102. The pusher 104 may be displaced a distance sufficient to locate the shoulder 114 of the pusher proximal to the hole 160 through the shaft 6. Thereafter, the lock-out 150 may be attached to the instrument by pushing the clip fingers onto the shaft 6 with the pin 158 extending through the hole 160 and into the internal channel 162 between the fasteners 30 and the pusher shoulder 114. Once the lock-out is attached, the follower 34 may be released so that the spring 102 drives the pusher in the distal direction until the shoulder 114 engages the pin 158 to prevent further advancement of the pusher toward the stack of fasteners 28. When engaged by the pin 158, the pusher 104 is spaced an appropriate distance from the stack of fasteners so that the follower does not apply a preload to the fasteners.

In one embodiment, a tether may be attached to the pusher 104 and extend in the proximal direction along the elongated shaft 6 to a location where it is accessible and can be used to retract the follower away from the fasteners to facilitate attachment of the lock-out. The tether may extend through and exit the proximal end of the handle 4 with a sufficient length of the tether available for grasping and pulling the pusher proximally. After the lock-out has been attached to the shaft, the tether may be detached and removed from the instrument.

Figure 14:
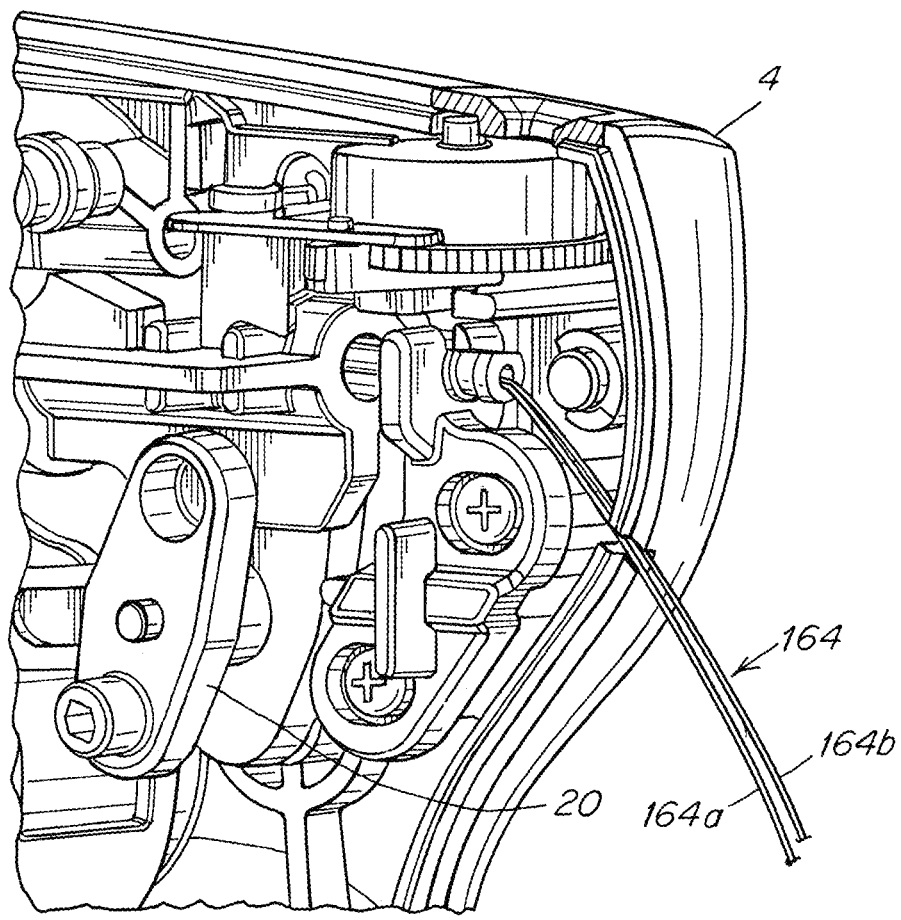
FIG. 14 is a schematic perspective view of a tether for retracting the follower extending from the proximal end of the handle.

In one embodiment, the tether 164 may be looped through the pusher with two segments of the tether extending from the pusher and exiting the handle 4, as shown in FIG. 14. After the lock-out clip has been attached, one segment 164a of the tether may be pulled proximally and to draw the other segment 164b of the tether distally through the handle, the shaft, the pusher and eventually proximally back through the shaft and the handle to remove the tether from the instrument.

The lock-out 150 may be formed as a one-piece component although any suitable arrangement may be employed. The pin 158 may be a separate component which is integrated with the clip. For example, in one embodiment, the pin 158 may be insert molded to the grip 154. Such an arrangement allows the use of a pin fabricated from a relatively stronger material, such as a metal, as compared to the clip, which may be formed of a plastic material.

In one embodiment, the clip fingers 152 and the grip body 154 may be integrally formed of a polycarbonate resin, such as CALIBRE 2061-15 FC850122 available from Trinseo. The pin 158 may formed of 304 stainless steel, full hard per ASTM F899 and passivated per ASTM A967, and is insert molded with the clip material to provide a connection therebetween having a minimum pull-out force of 5 lbf. However, it is to be understood that the lock-out may be fabricated from any suitable material, using any suitable technique, and/or to provide any suitable pull-out force as should be apparent to one of skill in the art.

Figure 15:
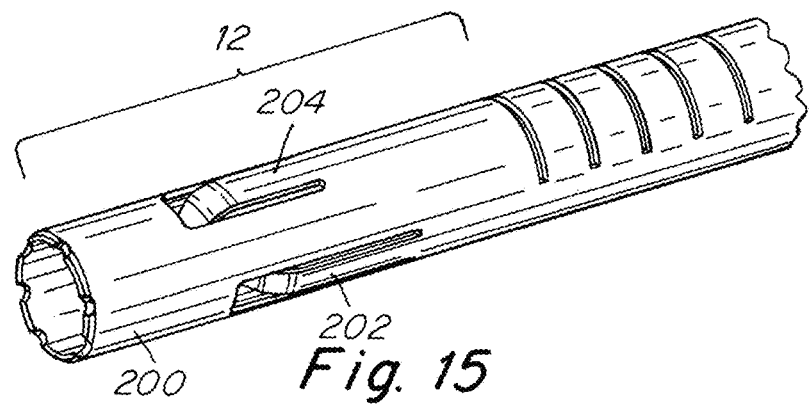
FIG. 15 is a schematic perspective view of the rigid straight portion including first and second restraints.
Figure 16:
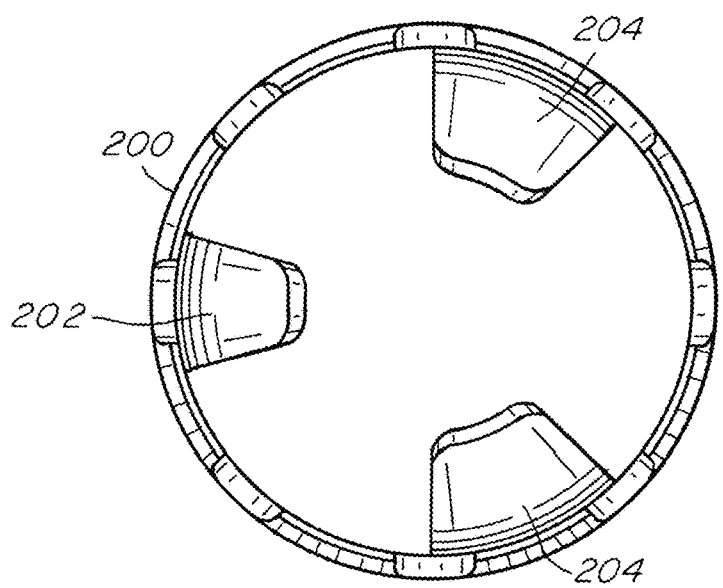
FIG. 16 is a schematic end view of the rigid straight portion depicted in FIG. 15.
Figure 17:
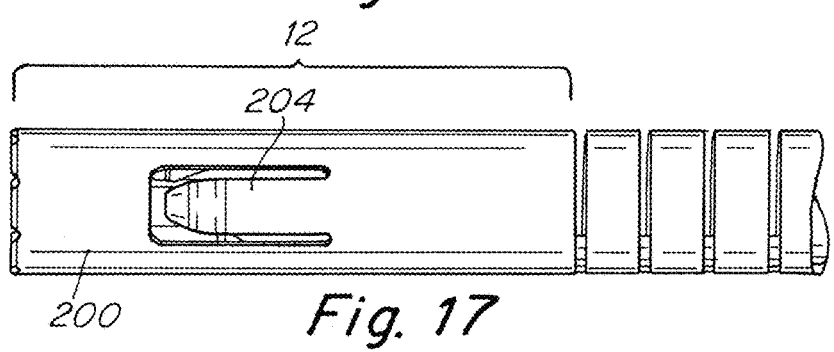
FIG. 17 is a schematic side view of the rigid straight portion depicted in FIG. 15.

FIGS. 15-18 depict an inner tubular member 200 which is a component of the elongated shaft 6. The inner tubular member 200 includes the rigid straight portion 12 which forms the distal end of the elongated shaft 6. The inner tubular member may also include one or more first restraints 202 and one or more second restraints 204 located within the rigid straight portion 12. As depicted in FIG. 15, the two second restraints 204 are distally located relative to a first restraints 202. The first restraint may be adapted and arranged to provide the first restraining force to the stack of fasteners during actuation. Correspondingly, the second restraints 204 may be adapted and arranged to provide the second restraining force to the stack fasteners during actuation. As noted previously, the first restraining force may be less than the second restraining force. The different restraining forces may be provided in any number of ways as the current disclosure is not limited to the manner in which the restraining forces are applied to the stack of fasteners. In some embodiments the restraints may be integrally formed with elongated shaft, or a component of the elongated shaft. Alternatively, the restraints may be formed separately and assembled with elongated shaft in any appropriate fashion including, but not limited to, welding, soldering, brazing, adhesives, interference fits, and fasteners.

The different first and second restraining forces may be provided in any appropriate manner. For example, in one embodiment, different compliances of the first and second restraints may be used to provide the different first and second restraining forces. More specifically, the second restraints may be less compliant than the first restraints. In another embodiment, the different first and second restraining forces may be provided using different numbers of the first and second restraints. In such an embodiment, a greater number of the second restraints may be used as compared to the number of first restraints. While specific methods of providing the different restraining forces have been noted above, other ways of providing the restraining forces are also contemplated.

In one possible embodiment, and as depicted in FIGS. 15-18, the first and second restraints 202 and 204 may correspond to tabs that extend inwards and distally relative to the inner tubular member 200 of the elongated shaft. To provide the desired first and second restraining forces, a single more compliant first restraint 202 and two less compliant second restraints 204 are incorporated into the rigid straight portion 12 of the inner tubular member 200 of the elongated shaft. The tabs corresponding to the second restraints 204 may have reduced lengths and/or increased widths as compared to the tab corresponding to the first restraint 202. Without wishing to be bound by theory, this results in the second restraints 204 being less compliant than the first restraint 202. Consequently, due to the use of two less compliant tabs for the second restraints 204 as compared to a single more compliant tab for the first restraint 202, the depicted embodiment is adapted to provide a second restraining force that is greater than the first restraining force. It should be understood that while a particular arrangement of first and second restraints has been depicted in the figures and described above, other embodiments for providing the first and second restraining forces are also possible.

The interaction between the first restraints 202, the second restraints 204, the fasteners 30, and the driveshaft 26 of the fastener deployment system are illustrated by FIGS. 19A-19C depicting a series of cross-sections of a distal portion of the elongated shaft 6 during actuation of the fastener deployment system. Prior to actuation, a distally located fastener 30 is positioned in the fastener deployment position 206. The fastener deployment position 206 may be defined by the relative locations of the first restraints 202 and the second restraints 204. The first restraints 202 and the second restraints 204 may define the fastener deployment position by retaining the head 30a of a fastener 30 between them prior to actuation. Retaining a fastener 30 in the fastener deployment position 206 using the restraints 202 and 204 may beneficially prevent a fastener from inadvertently being displaced out of the elongated shaft 6 as well as providing a consistent position of a fastener for subsequent deployment. Upon actuation of the fastener deployment system, the driveshaft 26 is distally displaced resulting in the fastener drivers 120 applying a force to the fastener 30 located in the fastener deployment position 206. The applied actuation force is greater than the second restraining force provided by the second restraints 204 resulting in the distal displacement and deployment of the fastener as depicted in FIG. 19B. As noted above, the stack of fasteners may have a separate force applied to distally displace the stack of fasteners and position the next fastener in the fastener deployment position 206 for the next actuation cycle. As the driveshaft 26 is withdrawn in a proximal direction to reset the fastener deployment system for the next actuation cycle, the fastener drivers 120 deform around and past the head 30a of the fastener 30 located in the fastener deployment position 206, see FIG. 19C. As depicted in the figure, the tabs corresponding to the first and second restraints 202 and 204 may be arranged and adapted to resist proximal movement of a fastener 30 located distally from the restraints 202 and 204. Consequently, proximal movement of a fastener 30 located in the fastener deployment position 206 may be prevented by the first restraint 202 as the driveshaft is moved in the proximal direction. Once the driveshaft 26 has been fully moved in the proximal direction, the surgical instrument is ready to deploy the next fastener.

While the above described embodiments have been directed to a follower that is driven by the reciprocating action of a driveshaft in a proximal and distal direction, other embodiments are possible. For example, in one embodiment, the follower may be associated with a rotating driveshaft such that rotation of the driveshaft may result in a distal displacement of the follower and the associated fasteners disposed within the driveshaft. In another exemplary embodiment, the follower may be associated with another component of the fastener deployment system such that actuation of the fastener deployment system results in a distal movement of the follower. For example, the follower may be associated with the trigger 14, the rigid linkage 20, or the shuttle 22. Further, the follower may be directly, or indirectly, associated with any of the above components.

As noted previously, in addition to displacing the stack of fasteners to position the next fastener in the fastener deployment position, in some embodiments, it may be desirable to maintain a particular orientation of the fasteners within the elongated shaft. FIG. 20 depicts a schematic exploded view of the elongated shaft 6 and the driveshaft 26 which may be disposed within the interior of the elongated shaft 6. The depicted pattern of slots formed in the exterior of the elongated shaft 6 impart flexibility to the portion of the elongated shaft 6 corresponding to the articulable portion 8. In the depicted embodiment, the driveshaft includes an internal channel to accommodate one or more fasteners 30 disposed therein. The driveshaft 26 may also include a guide surface 136. The guide surface 136 may be any appropriate shape, and as depicted in the figure, may correspond to a flat extending along the axial direction of the driveshaft 26. The guide surface 136 may interact with a corresponding surface on the fasteners 30 to maintain an orientation of the fasteners while they are disposed within the driveshaft 26 and as the driveshaft reciprocates between a distal position and a proximal position during actuation. In addition to the guide surface 136, the driveshaft 26 may also include a fastener driver 120a that interacts with the corresponding surface on the fasteners 30 to maintain the orientation of a fastener 30 as it is positioned in the fastener deployment position.

In the depicted embodiment, a flat corresponding to the guide surface 136 is present on an internal surface of the internal channel of the driveshaft 26. Additionally, the guide surface 136 may optionally be present on an exterior surface of the driveshaft 26 as well. While a particular shape has been depicted for the guide surface 136, any appropriate shape or combination of features could be present on the driveshaft 26 to maintain an orientation of the fasteners 30 disposed therein. For example, the guide surface 136 may correspond to a protrusion, a groove, or any other appropriate shape. Further, the guide surface 136 may extend along any appropriate portion of the driveshaft 26. For example, the guide surface 136 may extend along a distal portion of the driveshaft, a flexible portion 122 of the driveshaft, a portion of the driveshaft corresponding to the stack of fasteners located within the driveshaft, or the entire length of the driveshaft as the current disclosure is not limited in this fashion.

Figure 21:
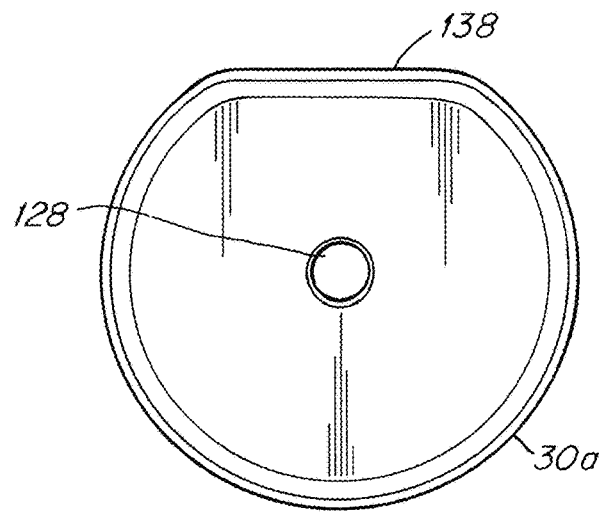
FIG. 21 is a schematic top view of a fastener.
Figure 22:
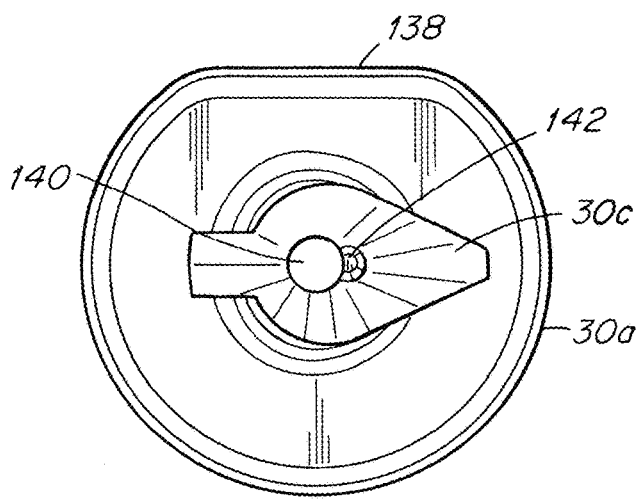
FIG. 22 is a schematic bottom view of the fastener depicted in FIG. 21.
Figure 23:
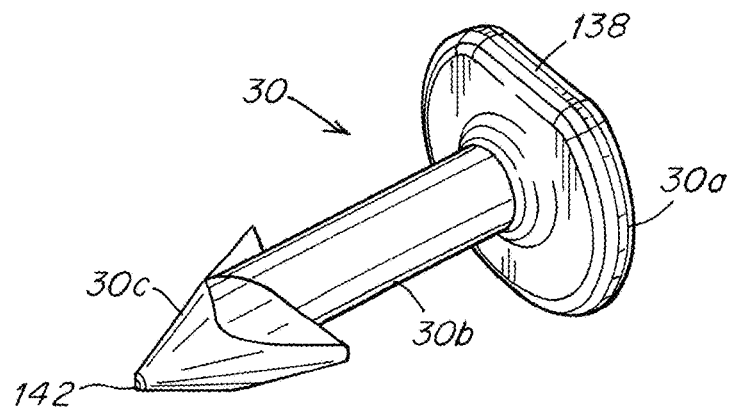
FIG. 23 is a schematic perspective view of the fastener depicted in FIGS. 21-22.

FIGS. 21-23 depict one possible embodiment of a fastener 30 for use with the driveshaft 26. The depicted embodiment of the fastener 30 includes: a head 30a; a shaft 30b extending from the head 30a; and a barbed end 30c located at a distal end of the shaft 30b. A surface 138 corresponding to the guide surface 136 of the driveshaft may be disposed on the head 30a. The surface 138 may be sized and shaped to complement the guide surface 136 the driveshaft such that the fastener 30 smoothly interfaces with the internal surfaces of the driveshaft 26. In the depicted embodiment, the surface 138 corresponds to a flat such that a cross-section of the head 30a includes a flat portion and a round portion sized and shaped to complement corresponding flat and round portions of a cross-section of the internal channel of the driveshaft. While the surface 138 corresponding to the guide surface 136 has been depicted as being located on the head 30a of the fastener, the surface 138 may be located on any appropriate portion of the fastener 30. For example, a portion of the shaft 30b or barbed end 30c could include a corresponding surface, or feature, that is shaped, sized, and arranged to interact with the guide surface 136 of the driveshaft to maintain an orientation of the fastener 30.

In addition to the surface 138 present on the fastener 30 which corresponds to the guide surface 136, the fastener 30 may also include a through hole 140 extending distally from a proximal surface of the head 30a through the shaft 30b and the barbed end 30c. The through hole 140 may be sized and shaped to accommodate the fastener guide, as described above, to maintain the alignment of the fasteners 30 within the elongated shaft. The through hole 140 may be centrally located, radially offset, or arranged in any other appropriate location as the current disclosure is not limited as to where the through hole 140 is located. While it may be desirable to include a through hole 140 to help maintain the alignment of the fasteners 30 within the elongated shaft, it may also be desirable in certain embodiments to provide a pointed tip 142 on the fastener as depicted in the figure. However, embodiments using a blunt tip and an associated piercing needle are also envisioned. To accommodate the through hole 140, the pointed tip 142 may be radially offset relative to the through hole 140.

Figure 24:
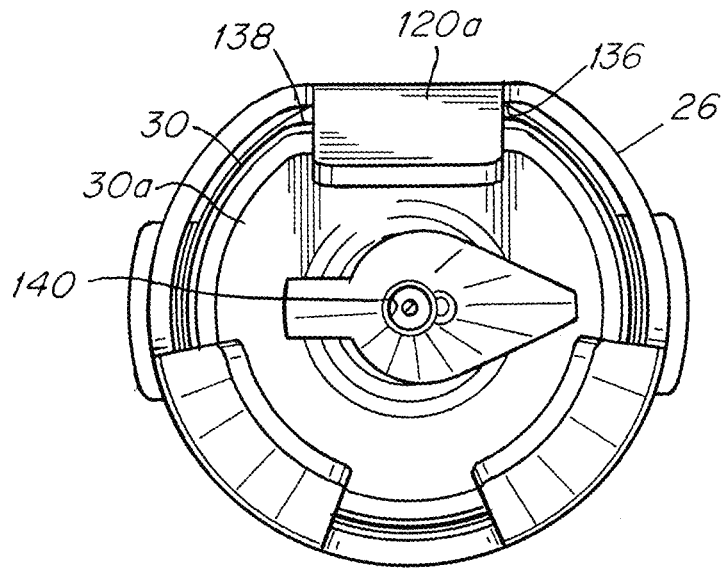
FIG. 24 is a schematic end view of the reciprocating driveshaft including a stack of fasteners disposed therein.

FIG. 24 depicts a distally located fastener 30 disposed within the internal channel 140 of the driveshaft 26. As illustrated by the figure, guide surface 136 and the fastener driver 120a of the driveshaft 26 are aligned with the corresponding surface 138 of the fastener 30. Due to the interaction of the flat portions of the internal channel cross-section and the fastener head (i.e. the guide surface 136 and corresponding surface 138), as well as the round portions of the internal channel cross-section and the fastener head, the fastener 30 may be maintained in a preselected orientation throughout the length of the driveshaft 26.

Figure 25:
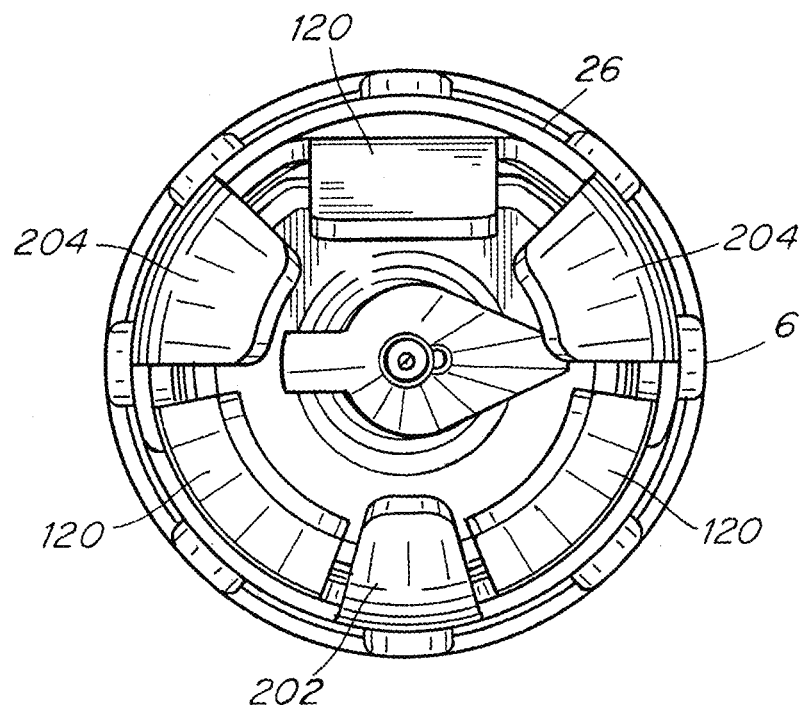
FIG. 25 is a schematic end view of the elongated shaft with the reciprocating driveshaft and stack of fasteners disposed therein.

FIG. 25 depicts the fastener 30 and driveshaft 26 of FIG. 24 disposed within the elongated shaft 6. As best illustrated by FIG. 19B, in some embodiments, the fastener drivers 120 may extend distally relative to the first and second restraints 202 and 204 when the driveshaft 26 is distally displaced to deploy a fastener. Consequently, it may be desirable to arrange the fastener drivers 120 and the first and second restraints 202 and 204 such that they do not interfere with one another during distal displacement of the driveshaft. In the depicted embodiment, the fastener drivers 120 are arranged in a triangular pattern at a distal end of the driveshaft 26 and the first and second restraints 202 and 204 are arranged in another corresponding triangular pattern around the internal surface of the elongated shaft 6 such that the fastener drivers 122 do not interfere with the first and second restraints 202 and 204 during the distal displacement of the driveshaft. It should be understood that while a particular number and arrangement of the fastener drivers and restraints has been depicted in the figures and described herein, the current disclosure is not limited in this manner. Instead, any appropriate number and arrangement of fastener drivers and restraints may be used. Further, other appropriate types of fastener drivers and restraints may also be used.

As indicated above, the elongated shaft 6 may include an articulable portion 8. The articulable portion may be articulated between a first position, such as an unarticulated (i.e. straight) position, and a second position, such as a fully articulated position, using the articulation control 10. In some embodiments, the articulable portion 8 may be articulated only between the first and second positions. In other embodiments, the articulable portion 8 may be articulated to one or more preselected articulated positions, or any arbitrary (i.e. not preselected) articulated position as the current disclosure is not limited in this fashion. Further, depending upon the embodiment, the articulable portion 8 may only be articulated in one direction, or it may be articulated in two directions. For example, the articulable portion 8 may be articulated between approximately 0° and 90°, 0° and 45°, −90° and 90°, −180° and 180° or any other appropriate range of angles. In addition, in some embodiments the articulable portion 8 may articulate about two different axes (e.g. articulation in the horizontal direction and vertical direction).

Figure 18:
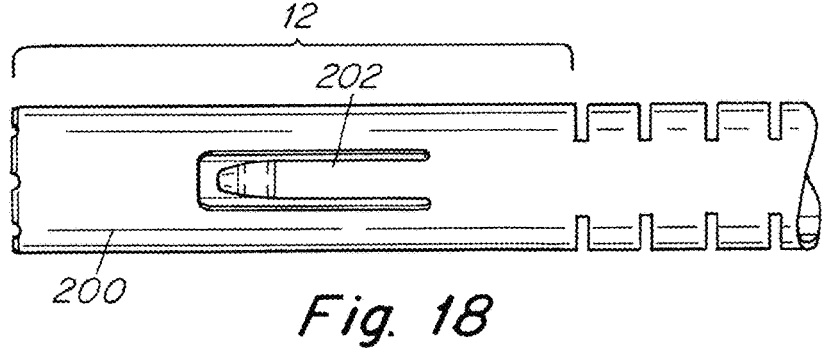
FIG. 18 is a schematic side view of the rigid straight portion depicted in FIG. 17 rotated 120°.

In some embodiments, it may be desirable to rotate the elongated shaft 6 to facilitate positioning of the distal tip. One such embodiment is depicted in FIGS. 1 and 18. The rotation of the elongated shaft 6 may be provided in any appropriate manner. For example, the elongated shaft 6 may simply be adapted to be rotatable to at least a portion of the handle 4. Alternatively, a portion of the handle 4 including the elongated shaft 6 may be rotatable relative to another portion of the handle 4, such as the portion including the grip. One such embodiment is depicted in FIG. 1. In the depicted embodiment, the surgical instrument 2 includes a first handle portion 16 and a second handle portion 18 including the elongated shaft 6. The first and second handle portions 16 and 18 may be constructed and arranged in any appropriate fashion to be rotatable relative to one another. It should be understood that while a surgical instrument including a rotatable elongated shaft 6 or handle 4 is depicted in the figures, a surgical instrument including a unitary handle and/or an elongated shaft 6 that is stationary relative to the handle are also possible as the current disclosure is not limited in this manner.

In certain applications, it may be advantageous to include a rigid straight portion 12 distally located from the articulable portion 8. For example, and without wishing to be bound by theory, when a driveshaft applies a force to a fastener as it goes around a curve, the force applied by the driveshaft to a proximal portion of the fastener may not be aligned with the deployment direction of the fastener. This may result in a portion of the applied force being directed against a side of the elongated shaft 6. In contrast, when a driveshaft applies a force to a fastener along a straight section, the applied force is aligned with the deployment direction of the fastener. Thus, including a rigid straight portion 12 that distally extends from the articulable portion 8 for a given length may enable the driveshaft to apply a reduced actuation force to deploy the fastener since the applied actuation force may be aligned with the deployment direction. Further, applying an actuation force that is aligned with the deployment direction may also improve the consistency of fastener deployment as the surgical instrument is varied between different articulation angles. In addition to the benefits noted above, the rigid straight portion 12 may also incorporate other components or features to aid in the positioning and deployment of a fastener from the surgical instrument. While a surgical instrument 2 including a distal rigid straight portion 12 has been described herein, and depicted in figures, it should be understood that embodiments are also envisioned in which the articulable portion 8 extends all the way to the distal end of the elongated shaft 6 such that the surgical instrument does not include a distal rigid straight portion.

While the present teachings have been described in conjunction with various embodiments and examples, it is not intended that the present teachings be limited to such embodiments or examples. On the contrary, the present teachings encompass various alternatives, modifications, and equivalents, as will be appreciated by those of skill in the art. Accordingly, the foregoing description and drawings are by way of example only.

What is claimed is:

1. A surgical instrument comprising:
a handle;
an elongated shaft extending in a distal direction from the handle, the shaft including a distal end opposite the handle;
at least one fastener located within the elongated shaft;
a fastener deployment system configured to deploy the at least one fastener from the elongated shaft in response to actuation thereof, the fastener deployment system configured to apply a first load to the at least one fastener prior to actuation thereof and to apply a second load to deploy the at least one fastener in response to actuation thereof, the first load being less than the second load, the first load to be applied to maintain the at least one fastener in a fastener deployment position proximate the distal end of the elongated shaft and prevent movement of the at least one fastener in a proximal direction away from the distal end of the elongated shaft; and
a lock-out removably attached to the elongated shaft, the lock-out configured and arranged to prevent the fastener deployment system from applying the first load to the at least one fastener while the lock-out is attached to the elongated shaft.

2. The surgical instrument of claim 1, wherein the fastener deployment system is configured to apply the first load to a proximal end of the at least one fastener.

3. The surgical instrument of claim 2, wherein the fastener deployment system includes a follower configured to engage and apply the first load to the proximal end of the at least one fastener.

4. The surgical instrument of claim 3, wherein the lock-out includes a pin extending into an internal channel of the elongated shaft to obstruct distal movement of the follower.

5. The surgical instrument of claim 4, wherein the lock-out includes a shroud configured to shield the pin from external contact when the lock-out is removed from the elongated shaft.

6. The surgical instrument of claim 1, wherein the elongated shaft includes an exterior surface and the lock-out is removably attached to the exterior surface of the elongated shaft.

7. The surgical instrument of claim 6, wherein the lock-out includes at least one pair of opposed clips configured to receive the elongated shaft therebetween and engage the exterior surface.

8. The surgical instrument of claim 7, wherein the clips have a curved configuration to extend about the elongated shaft.

9. The surgical instrument of claim 7, wherein the lock-out includes a shroud configured to cover the opposed clips when the lock-out is attached to and/or removed from the elongated shaft.

10. The surgical instrument of claim 7, wherein the lock-out includes a grip configured to be grasped and pulled to detach the lock-out form the elongated shaft.

11. The surgical instrument of claim 10, wherein the grip is coupled to the opposed clips and extends in a radial direction away from the elongated shaft.

12. The surgical instrument of claim 10, wherein the grip and the opposed clips are formed as a unitary structure.

13. The surgical instrument of claim 6, wherein the lock-out includes a pin extending into an internal channel of the elongated shaft to obstruct distal movement of a component of the fastener deployment system.

14. The surgical instrument of claim 1, wherein the fastener deployment system includes a follower configured to be driven in the distal direction upon actuation of the fastener deployment system.

15. The surgical instrument of claim 1, wherein the at least one fastener is a tack.

16. The surgical instrument of claim 1, wherein the at least one fastener includes plurality of tacks arranged in a stacked configuration.

17. A surgical instrument comprising:
a handle;
an elongated shaft extending in a distal direction from the handle;
at least one fastener located within the elongated shaft;
a fastener deployment system configured to deploy the at least one fastener from the elongated shaft in response to actuation thereof, the fastener deployment system configured to apply a first load to a proximal end of the at least one fastener prior to actuation thereof, the fastener deployment system including a follower configured to engage and apply the first load to the proximal end of the at least one fastener, wherein the follower includes a spring, a pusher associated with a distal end of the spring and a driver associated with a proximal end of the spring, the pusher configured to engage and apply the first load to the proximal end of the at least one fastener; and
a lock-out removably attached to the elongated shaft, the lock-out configured and arranged to prevent the fastener deployment system from applying the first load to the at least one fastener while the lock-out is attached to the elongated shaft.

18. The surgical instrument of claim 17, wherein the lock-out prevents the pusher from engaging the at least one fastener.

19. The surgical instrument of claim 18, wherein the lock-out retains the pusher in a spaced relation away from the at least one fastener.

20. A method of operating a surgical instrument, the method comprising acts of:
(a) providing a surgical instrument including:
a handle,
an elongated shaft extending in a distal direction from the handle,
at least one fastener located within the elongated shaft,
a fastener deployment system configured to deploy the at least one fastener from the elongated shaft in response to actuation thereof, the fastener deployment system configured to apply a first load to the at least one fastener prior to actuation thereof, and
a lock-out attached to the elongated shaft to prevent the fastener deployment system from applying the first load to the at least one fastener, the fastener deployment system being retained in spaced relation away from the at least one fastener with the lock-out;
(b) detaching the lock-out from the elongated shaft whereby the fastener deployment system applies the first load to the at least one fastener by permitting the fastener deployment system to move into engagement with the at least one fastener upon detachment of the lock-out; and
(c) following act (b), actuating the fastener deployment system to deploy the at least one fastener from the elongated shaft.

21. The method of claim 20, wherein act (a) includes applying zero load to the at least one fastener.

22. The method of claim 20, wherein act (b) includes maintaining the at least one fastener at a fastener deployment position located at a distal end of the elongated shaft by applying the first load thereto.

23. The method of claim 20, wherein the at least one fastener includes a plurality of fasteners arranged in a stack along the elongated shaft, the first load being applied to the stack of fasteners following detachment of the lock-out during act (b).

24. A method of operating a surgical instrument, the method comprising acts of:
(a) providing a surgical instrument including:
a handle,
an elongated shaft extending in a distal direction from the handle,
at least one fastener located within the elongated shaft,
a fastener deployment system configured to deploy the at least one fastener from the elongated shaft in response to actuation thereof, the fastener deployment system configured to apply a first load to the at least one fastener prior to actuation thereof, and
a lock-out attached to the elongated shaft to prevent the fastener deployment system from applying the first load to the at least one fastener, the lock-out including a pin extending into an internal channel of the elongated shaft to obstruct distal movement of the fastener deployment system;
(b) detaching the lock-out from the elongated shaft whereby the fastener deployment system applies the first load to the at least one fastener by removing the pin from the internal channel resulting in distal movement of the fastener deployment system into engagement with the at least one fastener and applying the first load; and
(c) following act (b), actuating the fastener deployment system to deploy the at least one fastener from the elongated shaft.

25. The method of claim 24, wherein the lock-out includes a shroud, and act (b) includes shielding the pin with the shroud when the lock-out is detached from the elongated shaft.

26. The method of claim 24, wherein the lock-out includes a grip, and act (b) includes grasping and pulling the grip to remove the pin.

27. A method of operating a surgical instrument, the method comprising acts of:
(a) providing a surgical instrument including:
a handle,
an elongated shaft extending in a distal direction from the handle,
at least one fastener located within the elongated shaft, a fastener deployment system configured to deploy the at least one fastener from the elongated shaft in response to actuation thereof, the fastener deployment system configured to apply a first load to the at least one fastener prior to actuation thereof, and a lock-out attached to the elongated shaft to prevent the fastener deployment system from applying the first load to the at least one fastener;

(b) detaching the lock-out from the elongated shaft whereby the fastener deployment system applies the first load to the at least one fastener; and (c) following act (b), actuating the fastener deployment system to deploy the at least one fastener from the elongated shaft by applying a second load thereto, the second load being greater than the first load.

28. A method of operating a surgical instrument, the method comprising acts of:

(a) providing a surgical instrument including:
a handle,
an elongated shaft extending in a distal direction from the handle,
at least one fastener located within the elongated shaft,
a fastener deployment system configured to deploy the at least one fastener from the elongated shaft in response to actuation thereof, the fastener deployment system configured to apply a first load to the at least one fastener prior to actuation thereof, the fastener deployment system including a follower configured to apply the first load to the at least one fastener, and
a lock-out attached to the elongated shaft to prevent the fastener deployment system from applying the first load to the at least one fastener, the lock-out being located between the follower and the at least one fastener during act (a);

(b) detaching the lock-out from the elongated shaft whereby the fastener deployment system applies the first load to the at least one fastener; and (c) following act (b), actuating the fastener deployment system to deploy the at least one fastener from the elongated shaft.

29. The method of claim 28, wherein the follower includes a spring, a pusher associated with a distal end of the spring and a driver associated with a proximal end of the spring, the spring being compressed between the pusher and the driver to produce the first load.

30. A surgical instrument comprising:
a handle;
an elongated shaft extending in a distal direction from the handle, the elongated shaft including an exterior surface, an internal channel and a hole extending from the external surface to the internal channel;
a stack of fasteners located within the internal channel of the elongated shaft;
a fastener deployment system configured to deploy at least one of the fasteners from the elongated shaft in response to actuation thereof, the fastener deployment system including a follower which includes a pusher configured to engage and apply a first load to the stack of fasteners; and
a lock-out clip removably attached to the exterior surface of the elongated shaft, the lock-out clip including a pin extending through the hole in the elongated shaft and into the internal channel of the elongated shaft, the pin located between the stack of fasteners and the pusher to prevent the pusher from applying the first load to the stack of fasteners while the lock-out is attached to the elongated shaft.

31. The surgical instrument of claim 30, wherein the fastener deployment system is configured to apply the first load to a proximal end of the stack of fasteners.

32. The surgical instrument of claim 30, wherein the follower further includes a spring and a driver, the pusher associated with a distal end of the spring and the driver associated with a proximal end of the spring.

33. The surgical instrument of claim 30, wherein the pin retains the pusher in a spaced relation away from the stack of fasteners.

34. The surgical instrument of claim 30, wherein the follower is configured to be driven in the distal direction upon actuation of the fastener deployment system.

35. The surgical instrument of claim 30, wherein the lock-out includes opposed clip fingers configured to receive the elongated shaft therebetween and engage the exterior surface.

36. The surgical instrument of claim 35, wherein the clip fingers have a curved configuration to extend about the elongated shaft.

37. The surgical instrument of claim 35, wherein the lock-out clip includes a grip configured to be grasped and pulled to detach the lock-out clip from the elongated shaft.

38. The surgical instrument of claim 37, wherein the grip is coupled to the opposed clip fingers and extends in a radial direction away from the elongated shaft.

39. The surgical instrument of claim 38, wherein the grip and the opposed clip fingers are formed as a unitary structure.

40. The surgical instrument of claim 30, wherein the stack of fasteners includes a plurality of surgical tacks.

* * * * *